United States Patent
Haverkost

(10) Patent No.: US 6,217,609 B1
(45) Date of Patent: Apr. 17, 2001

(54) IMPLANTABLE ENDOPROSTHESIS WITH PATTERNED TERMINATED ENDS AND METHODS FOR MAKING SAME

(75) Inventor: Patrick Alan Haverkost, Brooklyn Center, MN (US)

(73) Assignee: Schneider (USA) Inc, Plymouth, MN (US)

( * ) Notice: Subject to any disclaimer, the term of this patent is extended or adjusted under 35 U.S.C. 154(b) by 0 days.

(21) Appl. No.: 09/107,222

(22) Filed: Jun. 30, 1998

(51) Int. Cl.$^7$ .......................................................... A61F 2/06
(52) U.S. Cl. ................................................ 623/1.22; 623/1.13
(58) Field of Search .............................. 623/1, 1.15, 1.17, 623/1.2, 1.22, 1.35, 1.13

(56) References Cited

U.S. PATENT DOCUMENTS

| | | | |
|---|---|---|---|
| 4,816,028 | * 3/1989 | Kapadia et al. | 623/1 |
| 5,026,377 | 6/1991 | Burton et al. | 606/108 |
| 5,061,275 | 10/1991 | Wallsten et al. | 623/1 |
| 5,064,435 | 11/1991 | Porter | 623/12 |
| 5,127,919 | * 7/1992 | Ibrahim et al. | 623/1 |
| 5,219,355 | 6/1993 | Parodi et al. | 606/191 |
| 5,221,261 | 6/1993 | Termin et al. | 606/104 |
| 5,330,500 | 7/1994 | Song | 606/198 |
| 5,360,443 | 11/1994 | Barone et al. | 623/1 |
| 5,503,636 | * 4/1996 | Schmitt et al. | 606/200 |
| 5,575,818 | 11/1996 | Pinchuk | 623/1 |
| 5,607,466 | 3/1997 | Imbert et al. | 623/1 |
| 5,628,787 | 5/1997 | Mayer | 623/1 |
| 5,630,840 | 5/1997 | Mayer | 623/1 |
| 5,632,772 | 5/1997 | Alcime et al. | 623/1 |
| 5,645,559 | 7/1997 | Hachtman et al. | 606/198 |
| 5,653,684 | * 8/1997 | Laptewicz et al. | 604/22 |
| 5,667,486 | 9/1997 | Mikulich et al. | 604/8 |
| 5,676,696 | 10/1997 | Marcade | 623/1 |
| 5,709,713 | 1/1998 | Evans et al. | 623/1 |
| 5,713,917 | 2/1998 | Leonhardt et al. | 606/194 |
| 5,718,159 | 2/1998 | Thompson | 87/33 |
| 5,725,571 | * 3/1998 | Imbert et al. | 623/1 |
| 5,741,325 | * 4/1998 | Chaikof et al. | 623/1 |
| 5,741,333 | * 4/1998 | Frid | 623/12 |
| 5,755,772 | 5/1998 | Evans et al. | 623/1 |
| 5,824,036 | 10/1998 | Lauterjung | 623/1 |
| 5,849,037 | 12/1998 | Frid | 623/1 |
| 5,851,228 | 12/1998 | Pinheiro | 623/1 |
| 5,871,535 | * 2/1999 | Wolff et al. | 623/1 |
| B1 4,655,771 | 9/1996 | Wallsten | 623/1 |

FOREIGN PATENT DOCUMENTS

| | | |
|---|---|---|
| 0183372A1 | 6/1986 | (EP) . |
| 0621015A1 | 10/1994 | (EP) . |
| 0684021A1 | 11/1995 | (EP) . |
| 0740928A2 | 11/1996 | (EP) . |
| 0897698A2 | 2/1999 | (EP) . |
| 2737969 | 2/1997 | (FR) . |
| WO96/29955 | 10/1996 | (WO) . |
| WO97/16133 | 5/1997 | (WO) . |

OTHER PUBLICATIONS

Silicone–Covered Expandable Metallic Stents in the Esophagus: An Experimental Study. K.F. Binmoeller et al. *Endoscopy* 1992: 24:pp. 416–420.

* cited by examiner

*Primary Examiner*—V. Millin
*Assistant Examiner*—Alvin Stewart
(74) *Attorney, Agent, or Firm*—Larkin, Hoffman, Daly & Lindgren, Ltd.; Frederick W. Niebuhr; Andrew D. Ryan

(57) ABSTRACT

The invention relates to a braided implantable endoprosthesis such as a stent or stent-graft with selectively terminated elongated member ends to aid orientation and control. A saw-tooth or crown pattern is formed on an end or on an edge of an opening in the generally tubular body. The pattern is defined by a series of terminus on the elongated members at a predetermined distance from respective control points. The termini cooperate with the control points and provide layers when constrained. The invention also relates to methods of making a braided implantable endoprosthesis with patterned terminated ends.

29 Claims, 23 Drawing Sheets

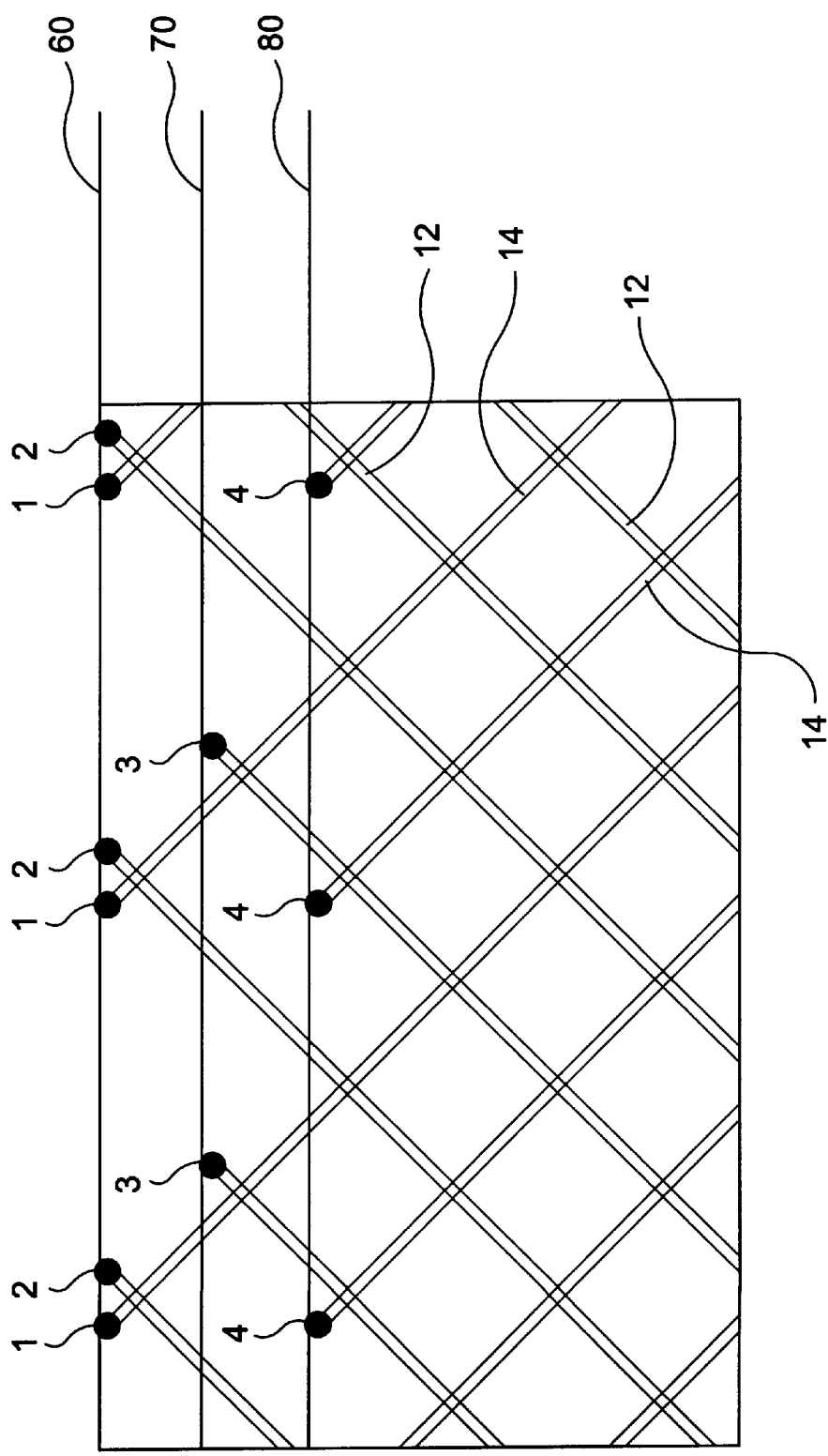

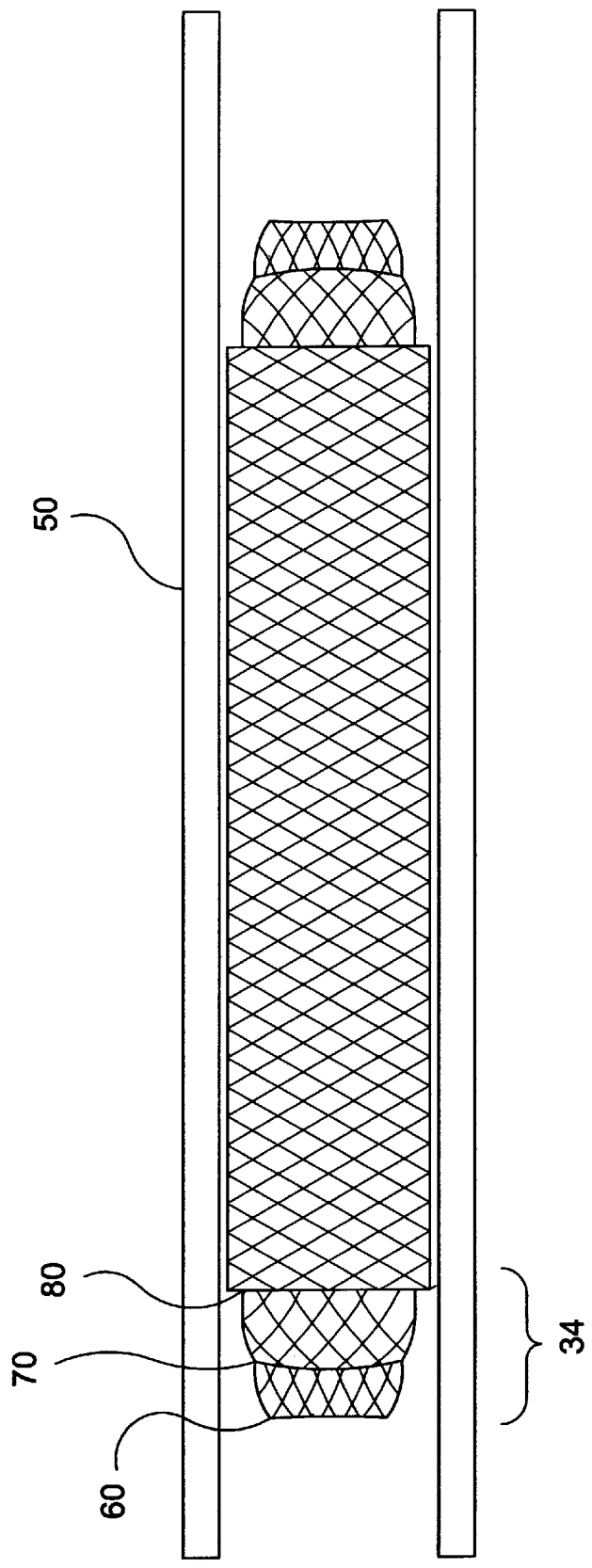

IMPLANTABLE ENDOPROSTHESIS WITH PATTERNED TERMINATED ENDS AND METHODS FOR MAKING SAME

1. Field of the Invention

This invention relates to a braided implantable endoprosthesis with patterned terminated ends and a method for making a braided implantable endoprosthesis using a trimline to maximize elongated member end orientation and to aid member crossing control during constrainment. More particularly, the invention relates to a stent or stent-graft having ends or openings with a crown or saw-tooth shape to enable efficient deployment or recapture thereof in a delivery device.

2. Background of the Disclosure

U.S. Pat. No. 5,221,261, entitled, *Radiably Expandable Fixation Member*, discloses an open weave fixation device secured to a distal end of a catheter or other diagnostic or treatment device, for either temporarily or permanently fixing the device within a body cavity.

U.S. Pat. No. B1 4,655,771, entitled, *Prosthesis Comprising Expansible or Contractile Tubular Body*, discloses a prosthesis comprising a flexible tubular body for transluminal implantation.

U.S. Pat. No. 5,026,377, entitled, *Stent Placement Instrument and Method*, discloses an instrument for the deployment or retraction of a self-expanding stent in body canal.

U.S. Pat. No. 5,061,275, entitled, *Self-Expanding Prosthesis*, discloses a resilient, elastic self-expanding prosthesis comprising a flexible tubular body.

U.S. Pat. No. 5,064,435, entitled, *Self-Expanding Prosthesis Having Stable Axial Length*, discloses a body implantable stent that consists of two or more generally tubular coaxial and slidably connected stent segments. The axially outward and non-overlapping portions of the stent can be designed for secure fixation to the tissue wall segment, for example, as radially outward flares.

U.S. Pat. No. 5,607,466, entitled, *Catheter With a Stent*, discloses a catheter with a self-expanding stent of a permeable mesh of stiff intersecting fibers.

U.S. Pat. Nos. 5,628,787 and 5,630,840, entitled, *Clad Composite Stent*, discloses a body compatible stent formed of multiple filaments arranged in two sets of oppositely directed helical windings interwoven with one another in a braided configuration. Each of the filaments is a composite including a central core and a case surrounding the core.

U.S. Pat. No. 5,645,559, entitled, *Multiple Layer Stent*, discloses a radially self-expanding stent having multiple layers.

U.S. Pat. No. 5,653,684, entitled, *Catheter With Expandable Member Mesh Tip*, discloses a catheter with a flexible-member mesh tip movably attached at a distal end of the catheter.

U.S. Pat. No. 5,667,486, entitled, *Prostatic Stent*, discloses a prostatic stent. The proximal section has a shape conforming to the neck of the urinary bladder.

U.S. Pat. No. 5,718,159, entitled, *Process for Manufacturing Three-Dimensional Braided Covered Stent*, discloses a prosthesis having a flexible tubular three-dimensionally braided structure of metal or polymeric non-filaments, and polymeric multifilament yarns.

U.S. Pat. No. 5,741,333, entitled, *Self-Expanding Stent For A Medical-Device To Be Introduced Into A Cavity Of A Body*, discloses a self-expanding stent.

European published patent application EP 0 740 928 A2 discloses a self-expandable stent with paired members.

The referenced patents disclosed herein are incorporated by reference in their entireties and made a part hereof for all purposes.

SUMMARY OF THE INVENTION

The present invention optimizes elongated member orientation and control during the constrainment and expansion cycles of self-expanding braided stents and stent-grafts. Use of the crown trim method principles may be applied to a braided implantable endoprosthesis having braid pattern configurations greater than 1-over-1-under. The invention includes trimming elongated member ends at predetermined termini in order to provide an optimum trim length at a point on the elongated member where each predetermined terminus terminates control over another member, for example, a certain crossing point. When trimmed, a crown or saw-tooth-like pattern emerges as certain portions of the elongated members are removed from the endoprosthesis. The saw-tooth pattern is continued around the desired trim-line, for example, a circumference at one or more of the ends of the endoprosthesis.

The 1-over-1-under braid pattern configuration in a WALLSTENT® endoprosthesis works well for deployment/recapture. To achieve similar deployment and recapture performance for greater than 1-over-1-under braid configuration patterns, for example, 2-over-2-under; 2-over-1-under; 1-over-2-under; 3-over-3-under; 3-over-2-under; 2-over-3-under; 3-over-1-under; 1-over-3-under; 4-over-4-under; 4-over-3-under; 3-over-4-under; 4-over-2-under; 2-over-4-under; 4-over-1-under; 1-over-4-under; 5-over-5-under; 5-over-4-under; 4-over-5-under; 5-over-3-under; 3-over-5-under; 5-over-2-under; 2-over-5-under; 5-over-1-under; 1-over-5-under, treatment along a predetermined trim-line of at least one of the ends is preferred for smooth deployment and recapture. Other braid pattern configurations and combinations greater than 5-over-5-under are also envisioned.

The following definitions are used herein for reference and descriptive purposes in the application. Elongated members refers to wire, filaments, multistranded cables and yarns fashioned of synthetic or natural polymers including plastics, metals or composites having any generally cross-section or homogeneity including solid, cored, hollow or DFT sections. Resilient refers to any flexible material having a restoring capability if flexed less than required to permanently deform; for example, spring-like and self-supporting materials. Saw-toothed refers to generally triangular shaped teeth found on a saw and a pattern formed at the desired trim-line. Crown, crown-cut or crown-like refers to the saw-tooth-like shape of the termination patterns at the end portions or trim-line. Other configurations including corrugations, scallops, crenelations, serrations, notches and the like, whether repetitive or random, that provide the desired results are encompassed within the scope of saw-toothed or crown. Terminus refers to a certain point where an elongated member is cut. Termini refers to a series of more than one terminus.

For reference, a braid becomes a stent after annealing. Annealing of the braid relaxes the stresses in the members and sets the shape of the endoprosthesis. Braid angle refers to the included angle between interbraided members of the braid, in the axial orientation, prior to annealing. Filament crossing angle refers to the included angle of the stent after annealing.

The present invention provides a unique stepped layering of the elongated members, assuring that the terminus do not substantially contact the exterior tube wall when mounted, deployed or recaptured. Along a trim-line, the terminus distance to the applicable control point is minimized or optimized to ensure that each member is long enough to supply control or interaction to adjacent elongated members.

An advantage of the implantable endoprosthesis and the associated method described herein is generally reduced scraping and delivery system perforation and particulate generation.

In sum, the invention relates to a braided medical device such as an implantable endoprosthesis with patterned terminated ends including a first number of elongated members wound helically in a first common direction and crossing a second number of elongated members wound helically in a second common direction. The crossings of the first and second elongated members define an angle therebetween and a plurality of control points. The first and second elongated members are braided in a braid pattern greater than 1-over-1-under. A tubular body is formed of the first and second elongated members and has ends and a middle portion therebetween. The tubular body is constrainable to a reduced diameter size and is self-expandable to an increased diameter size. A passage at least partially through the tubular body extends in a longitudinal direction. At least a portion of a saw-tooth pattern is formed on at least one of the ends or on an edge of an opening in the tubular body. The saw-tooth pattern is defined by a series of termini on at least one of the first or second elongated members at a predetermined distance from respective control points. The implantable endoprosthesis may further include an opening defined by each end of the tubular body and an edge surrounding each opening. The control point may be defined by crossing of a first and second elongated members. An average distance measured from each terminus to each respective control point may be less than about one-half pic. An average distance measured from each terminus to each respective control point may be about a one-third pic. The saw-tooth pattern may be adapted to substantially orient a plurality of the elongated members in a substantially similar longitudinal direction when the implantable endoprosthesis is in a substantially constrained diameter size. The series of termini may be adapted to become substantially layered when the implantable endoprosthesis is in a substantially constrained diameter. The saw-tooth pattern may be adapted to align the first and second elongated members. The depth of the saw-tooth pattern measured from one of the ends may increase as a braid pattern increases. The 2-over-2-under braid pattern may have a depth of about 1 pic; the 3-over-3-under braid pattern may have a depth of about 2 pics; and the 4-over-4-under braid pattern may have a depth of about 3 pics. At least one of the first and second elongated members may include a plurality of elongated members formed substantially parallel or formed as wire, yarns, cable or braid. At least one of the first and second elongated members may include up to 10 elongated members. At least one of the first and second elongated members may have more resilient members than the other. The tubular body may have a greater diameter at one or more of the ends than the middle portion. The tubular body is made of at least one of a metal, plastic, bioabsorbable or other synthetic or natural materials. The tubular body may have a braid angle between about 65 degrees and 155 degrees. A preferred braid angle is 105° to 115° and an especially preferred filament crossing angle is 106° to 110° (after heat treatment). The tubular body may have different diameters and shapes along its length when self-expanded.

The invention also relates to a method of making a braided implantable endoprosthesis including: forming a first number of elongated members wound helically in a first common direction and crossing a second number of elongated members wound helically in a second common direction. The crossing of the first and second elongated members define at least an angle therebetween and a plurality of control points. The first and second elongated members are braided in a braid pattern greater than 1-over-1-under; forming a generally tubular body formed of the first and second elongated members and having ends and a middle portion therebetween. The tubular body is constrainable to a reduced diameter size and self-expandable to an increased diameter size; and forming at least a portion of a saw-tooth pattern on at least one of the ends or on an edge of an opening in the tubular body. The saw-tooth pattern is defined by a series of termini on at least one of the first or second elongated members at a predetermined distance from respective control points.

The invention also relates to a method of making an implantable endoprosthesis including: providing a self-expanding implantable endoprosthesis having a generally tubular body having ends and a middle portion. The tubular body is made of a first number of elongated members wound in a first common direction and crossing a second number of elongated members wound in a second common direction. The crossing of the first and second elongated members define at least an angle therebetween and a plurality of control points. The first and second elongated members are braided in a braid pattern configuration greater than 1-over1-under. The tubular body is constrainable to a reduced diameter and self-expandable to an increased diameter; identifying a trim-line through the tubular body; cutting the one or more elongated members at one or more termini that intersect the trim-line; and cutting the one or more elongated members at termini where the one or more elongated members do not substantially control another elongated member to form a substantially saw-tooth pattern along the trim-line. The method of making a implantable endoprosthesis may further include constraining the tubular body to orient one or more elongated members in a substantially longitudinal direction and in two or more layers, or disposing a graft on one or more surfaces, for example, inside, outside, interwoven, or combinations thereof on or about the implantable endoprosthesis. A covering layer of elastic material or braided graft material may surround the tubular wall on all or along a portion of the longitudinal length to prevent growth. An implantable endoprosthesis may be formed by a method of making a stent.

The invention also relates to a braided implantable endoprosthesis with patterned terminated ends including at least one set of resilient elongated members wound helically with another set of resilient elongated members in a braid pattern of at least 1-over-1-under and crossing at multiple control points forming a generally tubular body having one or more surfaces. The tubular body terminates in end portions and with a middle portion therebetween. The tubular body is constrainable to a reduced diameter size and is self-expandable to an increased unconstrained diameter size. The implantable endoprosthesis has at least a portion of a crown shaped termination pattern with a depth of at least 1 pic at one or more of the end portions. A crown shaped termination pattern at one or more of the end portions is defined by one or more termini located adjacent control points near the one or more end portions. The implantable endoprosthesis may further include a graft material disposed on at least a portion of the one or more surfaces of the tubular body.

The implantable endoprosthesis generally assumes a tubular form in an unloaded or expanded state when not subjected to external forces and is generally characterized by a longitudinal shortening upon radial expansion and a longitudinal lengthening upon radial contraction.

The implantable endoprosthesis generally includes 10–36 members braided into a tubular mesh configuration. Alternative designs could be made using more than 36 elongated members. Stents and stent-grafts are envisioned having as many as 500 elongated members and which are made with braiders having sufficient carrier capacity.

The implantable endoprosthesis, for example, a stent is preferably heat treated at about 500° C. to about 580° C. for about 1 to about 5 hours. An especially preferred heat treatment is at about 530° C. to about 550° C. for about 2 to about 3 hours.

The implantable endoprosthesis may be a stent, stent-graft, graft, filter, occlusive device, and valve. A graft may be made from materials such as polyethylene terephthalate (PET), expanded polytetrafluoroethylene (ePTFE), polycarbonate urethane (PCU) or polyurethane (PU). A graft may be made of braided, woven, dip-coated or spray-cast PET, PCU, or PU fibers. The graft may also be made of film, sheet, or tube such as an ePTFE or PCU material.

Several materials may be used to make the elongated members of the endoprosthesis, including, stainless "spring" steels, and certain cobalt-based alloys, more particularly, two alloys including cobalt, chromium, iron, nickel and molybdenum sold under the brand names "Elgiloy" (available from Carpenter Technology Corporation of Reading, Pa.) and "Phynox" (available from Metal Imphy of Imphy, France), respectively. Another suitable cobalt-chromium alloy is available under the brand name "MP35N" from Carpenter Technology Corporation of Reading, Pa. Drawn filled tubing (DFT) with core is available from Fort Wayne Metals Research Products Corporation of Ft. Wayne, Ind. Nitinol is commercially available from Shape Memory Applications, Inc. of Santa Clara, Calif. The elongated members can also be constructed of a biocompatible plastic, polypropylene, polyesters and polyurethanes.

Materials may also include members made of polylactide bioabsorbable polymer, helically wound and interwoven in a braided configuration. The members may also be made of poly(alpha-hydroxy acid) such as poly-L-lactide (PLLA), poly-D-lactide (PDLA), polyglycolide (PGA), polydioxanone, polycaprolactone, polygluconate, polylactic acid-polyethylene oxide copolymers, modified cellulose, collagen, poly(hydroxybutyrate), polyanhydride, polyphosphoester, poly(amino acids), or related copolymer materials.

Bioabsorbable resins such as PLLA, PDLA, and PGA are available from PURAC America, Inc. of Lincolnshire, Ill. Partially oriented yarns and flat yarns are commercially available from Wellman Inc. of Charlotte, N.C. The partially oriented yarns can be textured by Milliken, Inc. of Spartenburg, S.C. Silicone adhesive is commercially available from Applied Silicone of Ventura, Calif. Corethane is available from Corvita Corporation. The remaining materials discussed in the application are commercially available.

Useful tools to make the present invention include Erem cutters Model E503T; Measuring guide tube; Gardena Scissors Model 370; Stereo Microscope; Magnifying Lens; and Ruler.

Still other objects and advantages of the present invention and methods of construction and use of the same will become readily apparent to those skilled in the art from the following detailed description, wherein only the preferred embodiments are shown and described, simply by way of illustration of the best mode contemplated of carrying out the invention. As will be realized, the invention is capable of other and different embodiments and methods of construction and use, and its several details are capable of modification in various obvious respects, all without departing from the invention. Accordingly, the drawings and description are to be regarded as illustrative in nature, and not as restrictive.

BRIEF DESCRIPTION OF THE DRAWINGS

FIG. 16 is a schematic view of the crown trim pattern showing a series of terminus and elongated members;

FIG. 18 illustrates a side view of an endoprosthesis in a delivery tube with layers formed at the patterned terminated ends.

DETAILED DESCRIPTION OF THE INVENTION

Figure 1:
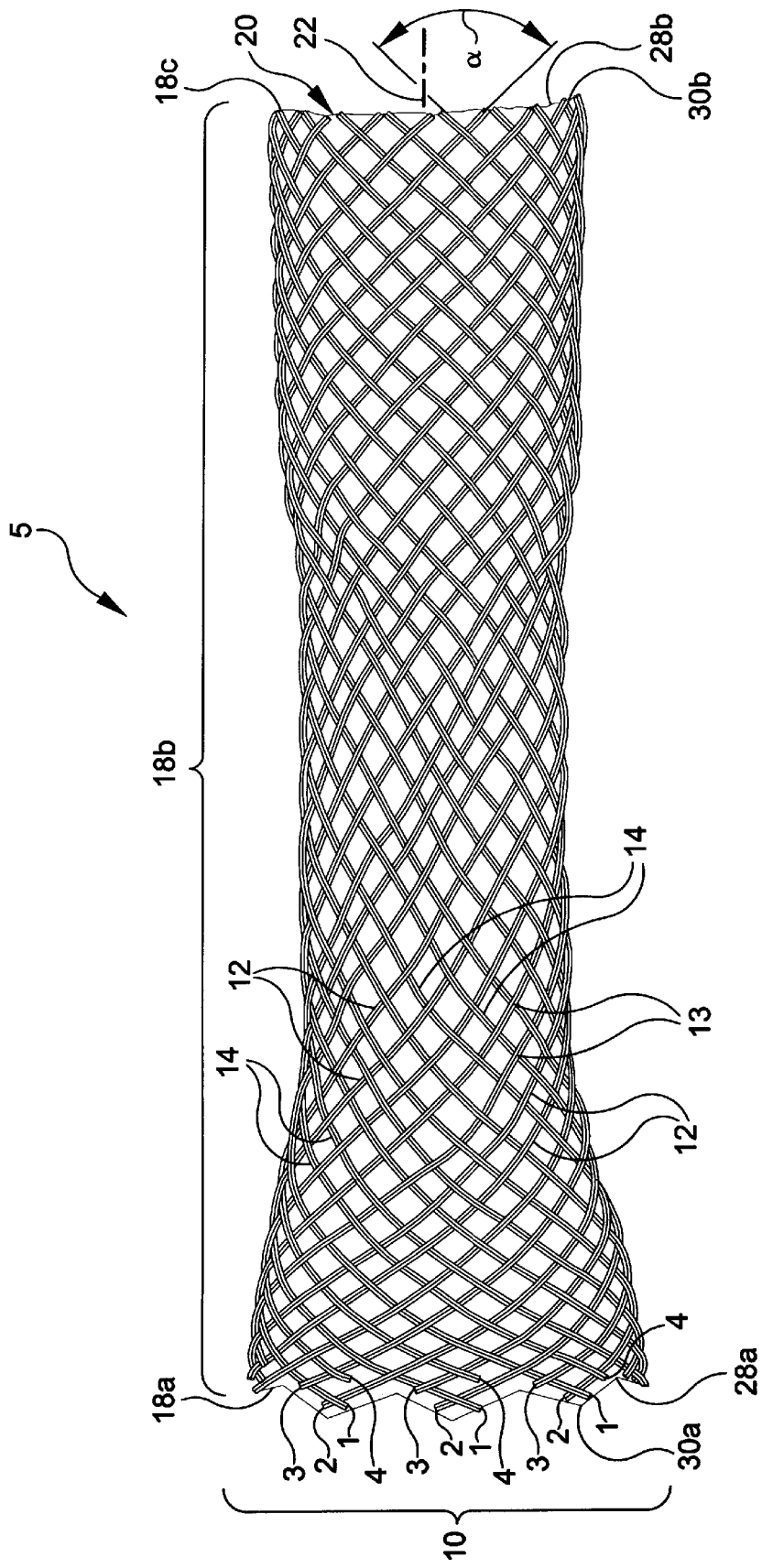
FIG. 1 is a side view of a stent-graft showing various shapes along a longitudinal length and showing a crown-cut termination pattern.

Reference is made to FIG. 1, illustrating a braided implantable endoprosthesis 5 having a patterned terminated end 10. A first number of elongated members 12 are wound helically about an axis 22 in a first common direction and cross a second number of elongated members 14 wound helically in a second common direction. The crossing 13 of the first and second elongated members 12, 14 defines an angle at the intersection and defines a plurality of control points 16 further shown in FIG. 15a and described below. The first and second elongated members 12, 14 are braided in a braid pattern greater than 1-over-1-under. The sets of members 12, 14 may be interwoven in a variety of over and under braided configurations to form multiple intersections or crossings 13.

The generally tubular body includes a middle portion 18b between the ends 18a, 18c. The implantable endoprosthesis 5 may include an edge 30a, 30b surrounding each opening 28a, 28b at one or more ends 18a, 18c. The tubular body is constrainable to a reduced diameter and is self-expandable to an increased diameter. A passage 20 is formed through at least a portion of the tubular body and extends in a longitudinal direction 22. The passage may close at an end 18a, 18c or at middle portions 18b. The endoprosthesis 5 may have various shapes as shown in FIG. 1. A taper may decrease, positively or negatively. The tubular body may have a greater diameter at one or more of the ends 18a, 18c than the middle portion 18b.

The first and second elongated members 12, 14 may include a plurality of elongated members formed substantially parallel and close to one another. The members 12, 14 may be axially displaced relative to each other. Adjacent parallel members 12, 14 may be tightly configured or be spaced apart from one another by about 1–2 millimeters (0.04–0.08 inches) when in a relaxed state. The first and second elongated members 12, 14 may include up to 10 elongated members close to one another or spaced apart. The first and second elongated members 12, 14 may have more resilient members in one set than the other.

A preferred embodiment includes a braided implantable endoprosthesis 5 with patterned terminated ends having at least one set of resilient elongated members 12, 14 wound helically with another set of resilient elongated members 12, 14 in a braid pattern of at least 1-over-1-under and crossing at multiple control points 16 forming a tubular body having one or more surfaces 42, 44. The tubular body terminates in end portions 18a, 18c and with a middle portion 18b therebetween. The tubular body is constrainable to a reduced diameter size and self-expandable to an increased unconstrained diameter size. The implantable endoprosthesis has a crown shaped termination pattern 24 with a depth of at least 1 pic at one or more of the end portions 18a, 18c. The crown shaped termination pattern 24 at one or more of the end portions 18a, 18c is defined by one or more termini 1, 2, 3, 4 and adjacent control points 16 near the one or more end portions 18a, 18c.

Figure 2:
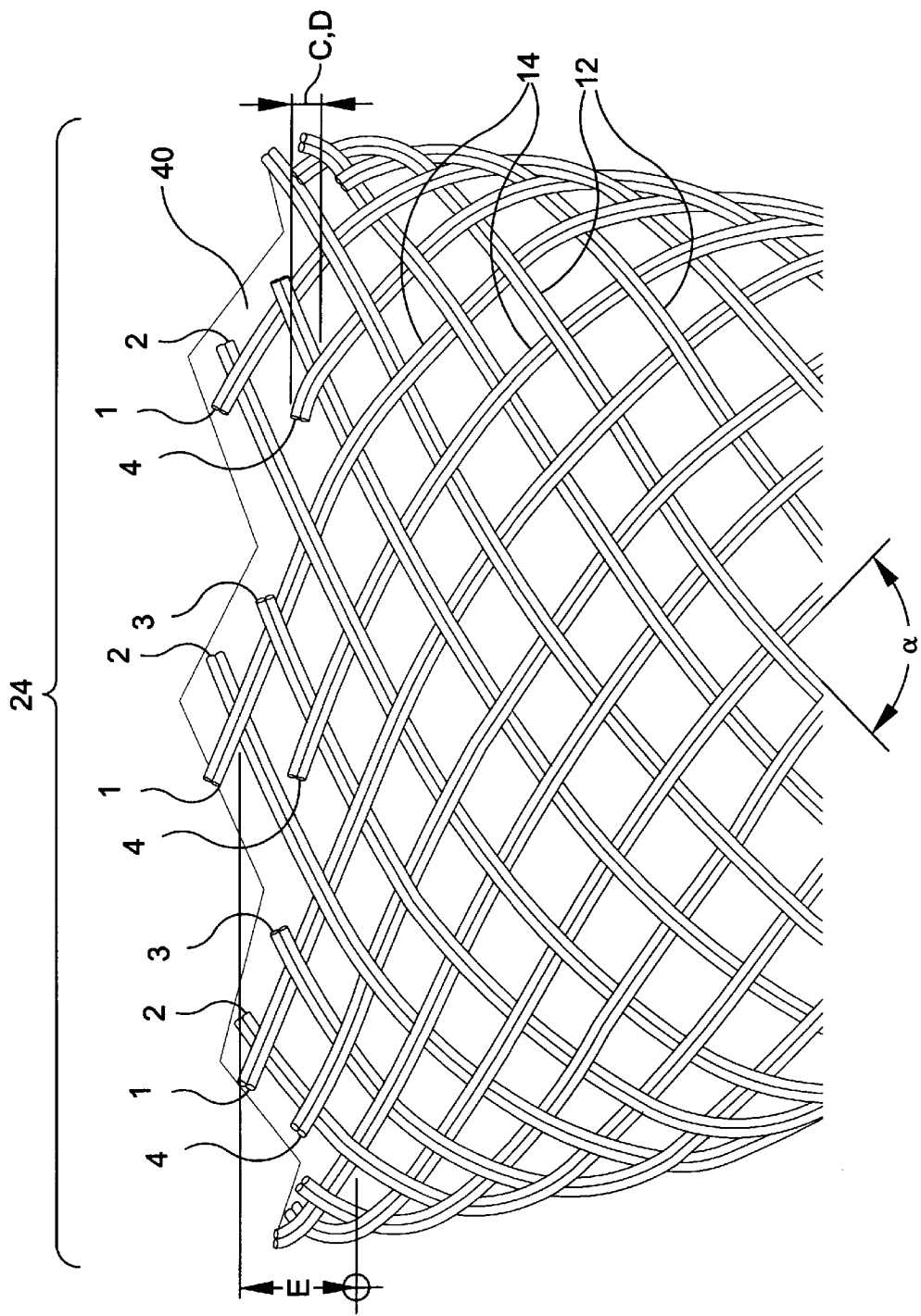
FIG. 2 is an enlarged view of the crown-cut from FIG. 1

FIG. 2 shows an enlarged view of the patterned terminated end 10 at end 18a on the endoprosthesis 5 of FIG. 1. The braid pattern configuration shown is 2-over-2-under with double members generally parallel and spaced close together. Shown is a radial outward taper and a graft 40 on the interior surface of the stent.

Figure 7B:
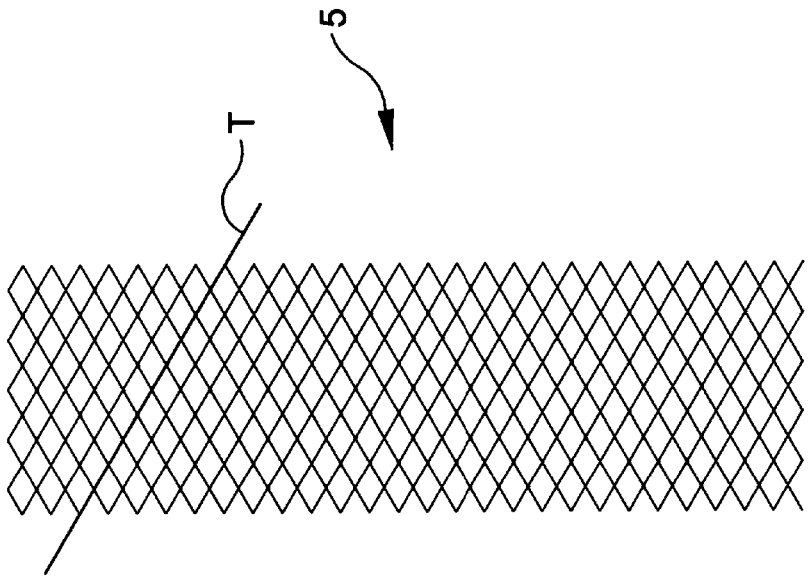
FIGS. 7a–7e are schematic side views of various embodiments of trim-lines on a stent or stent-graft.
Figure 7A:
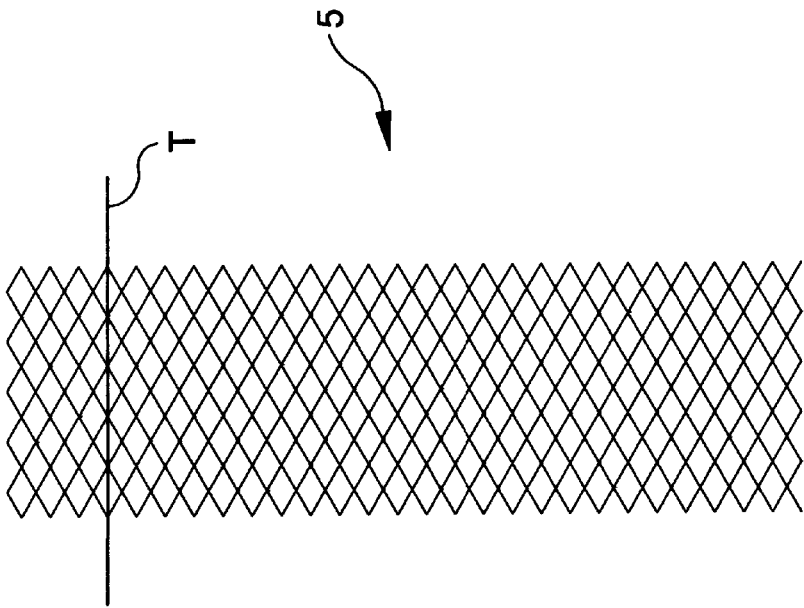
Figure 7D:
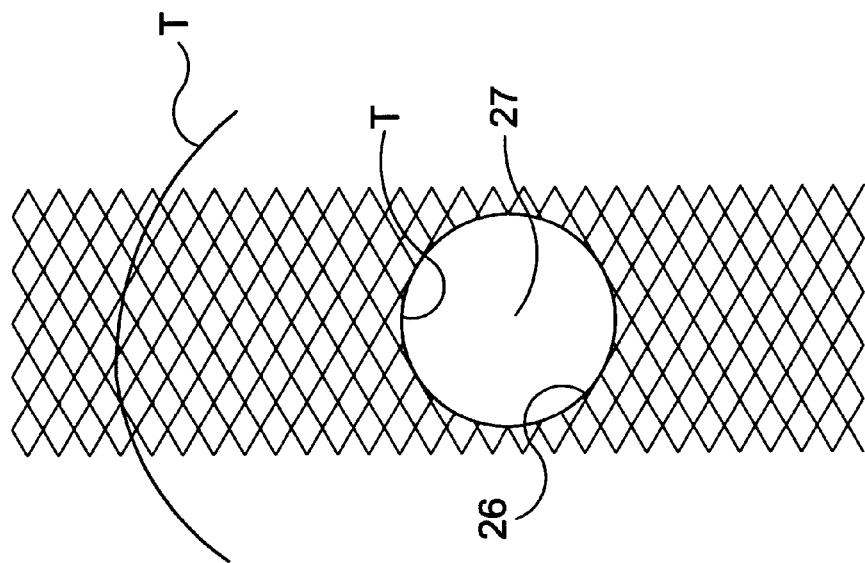

A saw-tooth pattern 24 is formed on at least one of the ends 18a, 18c or on an edge 26 of an opening 27 as shown, for example, in FIG. 7d. The saw-tooth pattern 24 is defined by a series of termini 1, 2, 3, 4 on at least one of the first or second elongated members 12, 14 at a predetermined distance from respective control points 16. Each control point 16 is located at a selected crossing 13 of a first and second elongated members 12, 14. A preferred average distance C measured from each terminus 1, 2, 3, 4 to each respective control point 16 is less than about one-half pic. An especially preferred average distance D measured from each terminus to each respective control point 16 is about a one-third pic.

The optimum trim length from a terminus 1, 2, 3, 4 of an elongated member 12, 14 from a control point is between about ¼ pic to about 0 pics. A depth E of the saw-tooth pattern 24 measured from one of the ends 18a, 18c generally increases as the braid pattern increases.

The saw-tooth pattern 24 generally orients and aligns the elongated members 12, 14 in a substantially similar longitudinal direction and in a generally layered configuration when the braided implantable endoprosthesis 5 is in a substantially constrained diameter.

The crown-trim method is used to cut one or more patterned terminated ends 10 or saw-tooth pattern 24 at ends 18a, 18c or at an edge 26 of an opening 27 on an endoprosthesis 5. Further descriptions of various trim patterns are shown in FIGS. 7a–7e. Cutting or trimming keeps the termini 1, 2, 3, 4 straighter when the braided stent 46 or stent-graft 48 is compressed in a delivery system 50. The saw-tooth or crown-cut pattern prevents members 12, 14 or wires from being curled, splayed or oriented radially outward.

The endoprosthesis 5 is illustrated in its relaxed state, i.e., in the configuration it assumes when subject to no external stresses. The members 12, 14 are resilient, permitting a radial compression of the stent into a reduced-radius, extended-length configuration suitable for transluminal delivery to the intended placement site. As an example, an endoprosthesis 5 can have a diameter of about ten millimeters in the relaxed state, and can be elastically compressed to a diameter of about 2 millimeters (0.08 inches) and have an axial length of about twice the axial length of the relaxed endoprosthesis 5. However, different applications call for different performance and diameters. Elongated members 12, 14 may have an average diameter ranging from about 0.00276 inches to about 0.031 inches. Endoprostheses are envisioned for all lumens in a body, preferred sizes range from about 2 mm to about 60 mm and generally any length.

Figure 3:
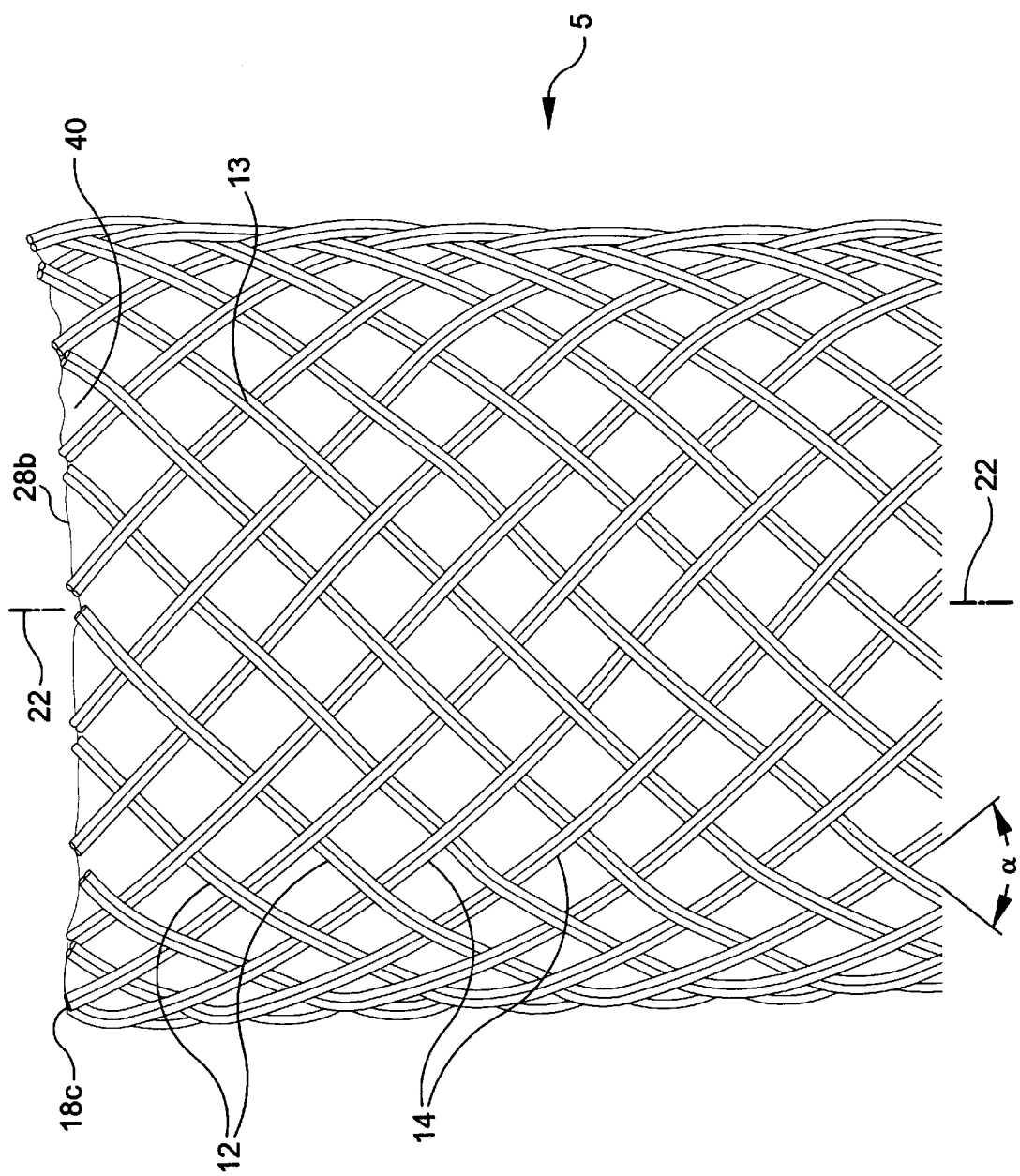
FIG. 3 is an enlarged view of a generally tubular body from FIG. 1.

FIG. 3 shows an enlarged view of end 18c without a patterned terminated end 10.

Figure 4:
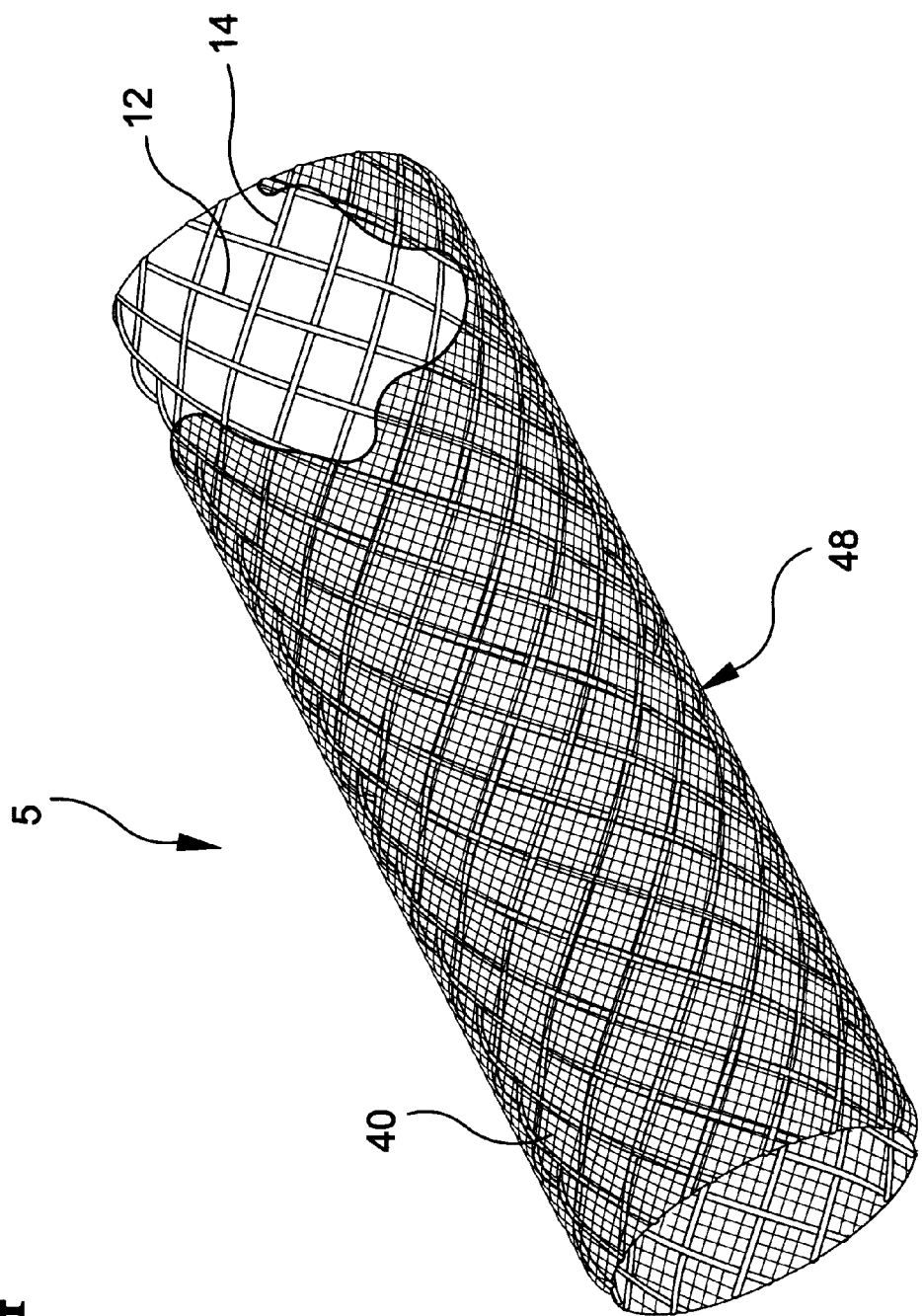
FIG. 4 is an isometric view of a stent-graft illustrating an exposed portion of the braided elongated members.
Figure 5:
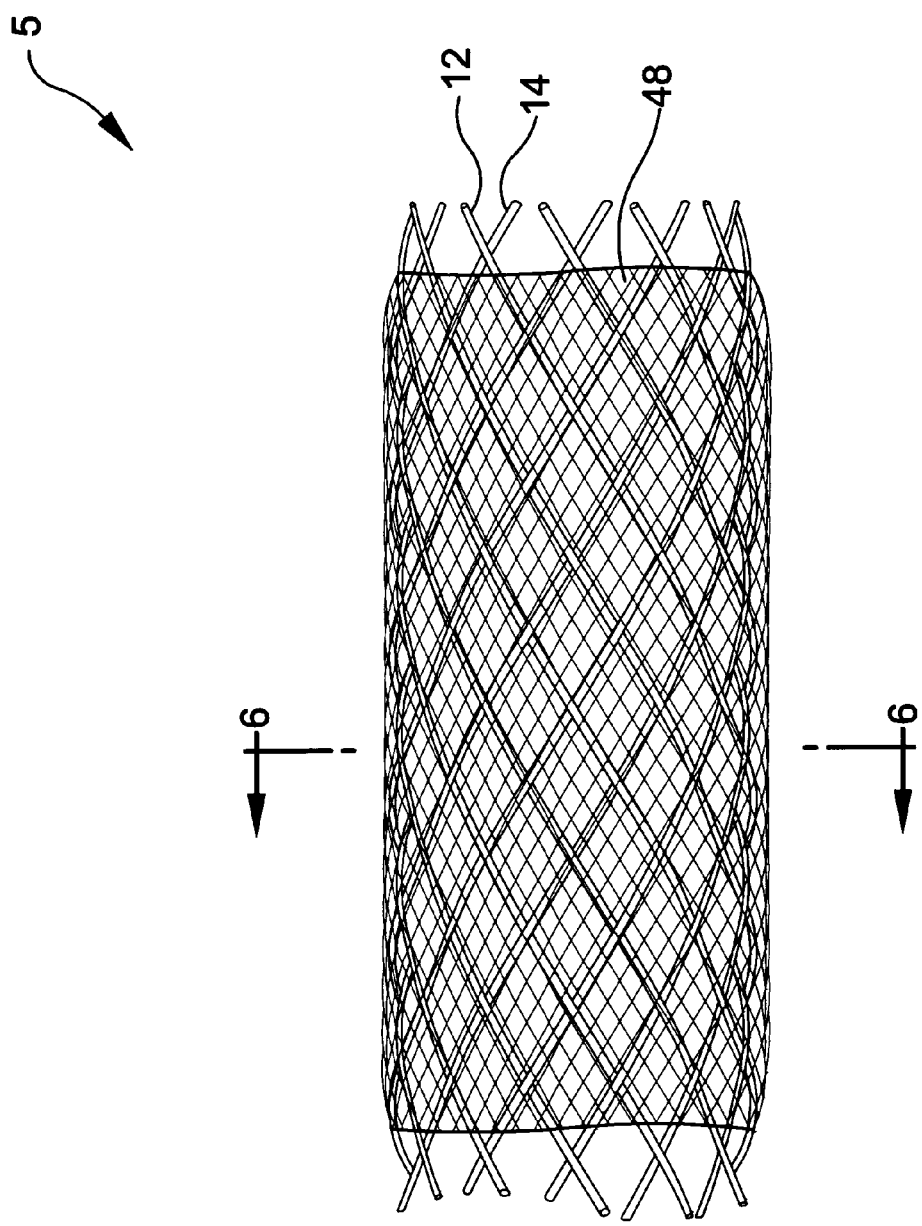
FIG. 5 is a side view of another embodiment of a stent-graft illustrating the graft disposed on a portion of the braided elongated members.
Figure 6B:
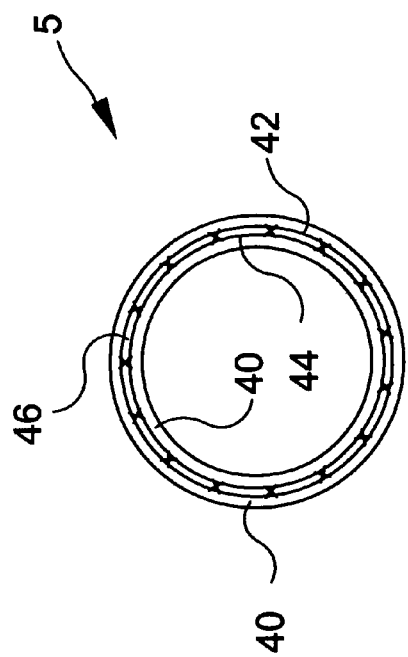
FIGS. 6a–6d are various embodiments of a stent-graft taken through 6—6 of FIG. 5.
Figure 6A:
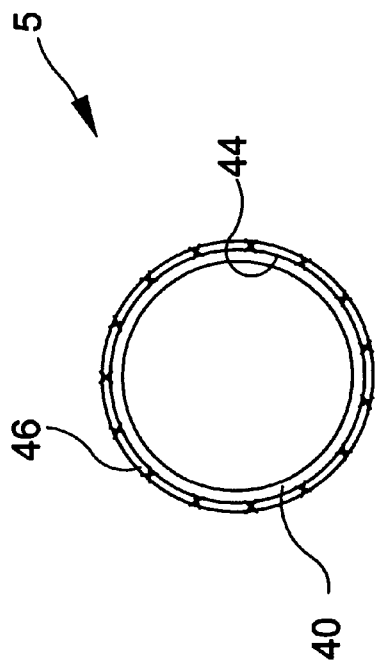
Figure 6D:
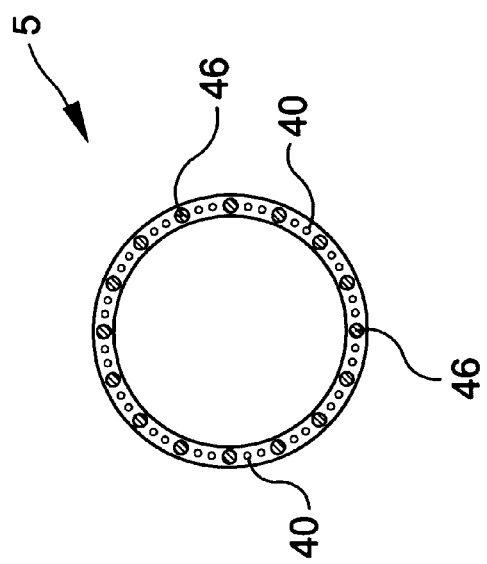
Figure 6C:
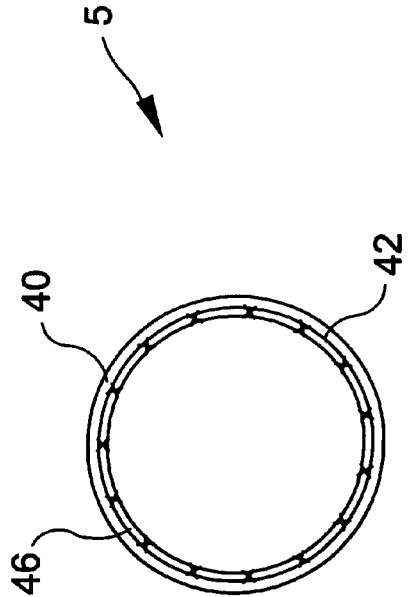

FIGS. 4 and 5 show examples of a graft 40 that may be used with the present invention. An endoprosthesis 5 is shown with a 1-over-1-under pattern, however, the present invention relates to an endoprosthesis 5 having greater than a 1-over-1-under braid pattern configuration. The figures are shown to represent a graft 40 and stent-graft 48. Also, the figures are shown to distinguish a 1-over-1-under braid pattern configuration from a greater than 1-over-1-under braid pattern configuration shown in other figures and discussed herein.

A separately manufactured and permanent graft 40 may be disposed on and adhered to at least a portion of the endoprosthesis 5 with an adhesive to form the stent-graft 48. The graft 40 generally radially expands and contracts with the stent 46. Vascular grafts are shown, for example, in U.S. Pat. No. 5,116,360. The graft 40 is preferably made of PET, ePTFE, PCU, or PU. Strands can be woven, braided, or knitted into a tubular fabric shape.

The graft 40 may surround the outside surface 42 or be surrounded by the inside surface 44 of the stent 46. In another embodiment, two grafts 40 may be used to surround and sandwich the stent 46. The filament crossing angle of the assembly generally determines the relationship between radial compression and axial elongation of the stent-graft 48. Smaller angles generally result in less axial shortening for a given amount of radial enlargement. The graft 40 is highly compliant and conforms to changes in the shape of the stent 46.

A primary consideration is to select a braid angle θ of the graft 40 with respect to a braid angle α of the stent 46, and to closely match the geometrical diameter and elongation properties of the stent 46 and graft 40 formed into the stent-graft 48 by about matching the respective braid angles.

A variety of methods and adhesives may be used for bonding the graft 40 to the stent 46. The adhesives include a PLLA material, however, other bioabsorbable materials may be used. A siloxane polymer (silicone) may be used as an adhesive. Other alternative polymers may include fluorosilicone and polycarbonate urethane. A wide range of sizes of the endoprosthesis 5 including lengths, diameters, and member diameters are envisioned.

FIGS. 6*a*–6*d* show various embodiments of a stent-graft in an unconstrained, radially expanded state taken through the line 6—6 of FIG. 5 illustrating the graft 40 disposed on the inside of the stent; inside and outside of the stent, outside of the stent, and interbraided or interwoven through the stent, respectively.

Figure 7C:
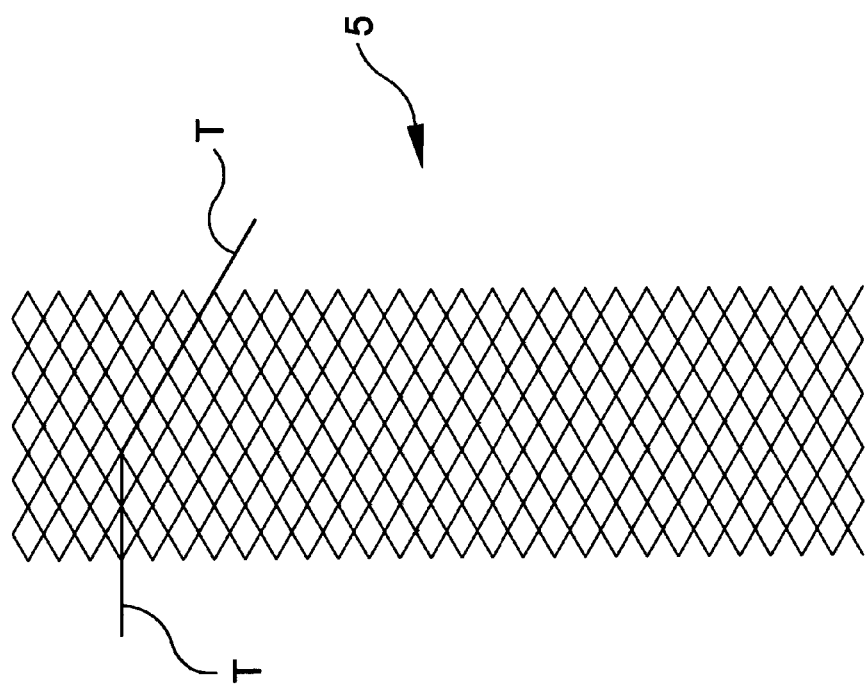
Figure 7E:
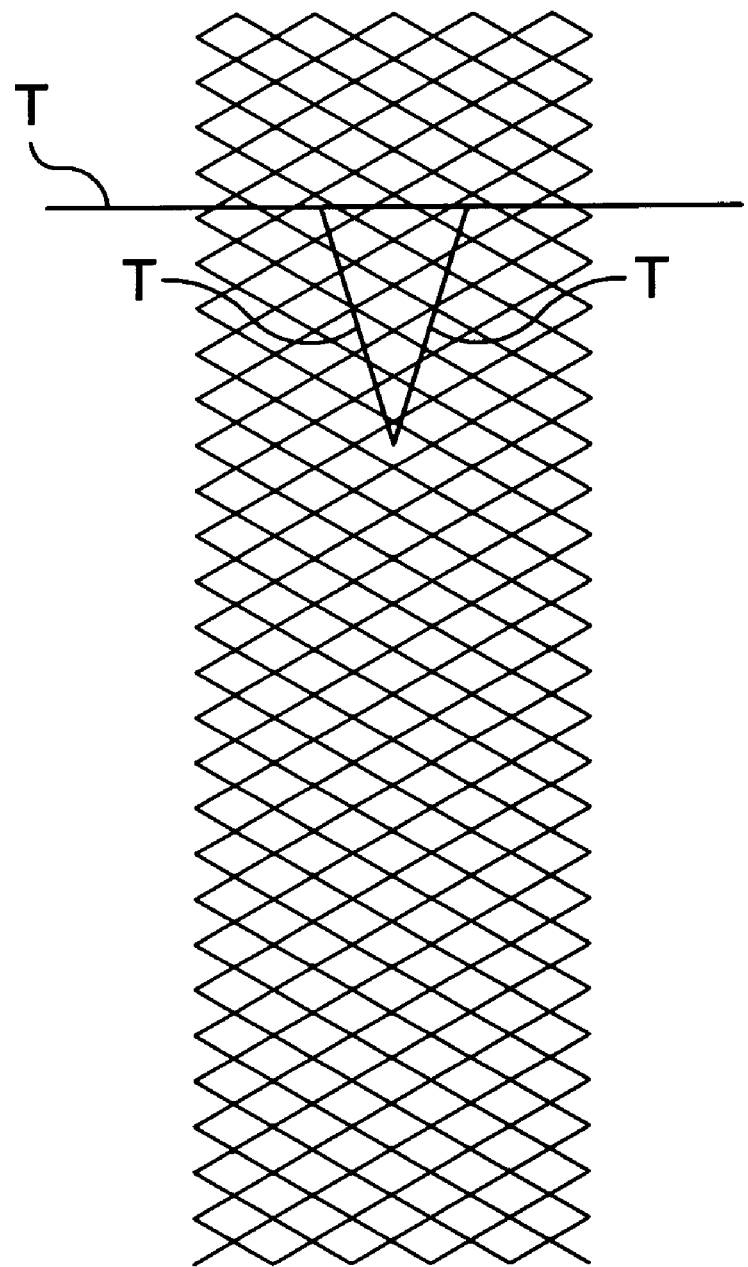

FIGS. 7*a*–7*e* show schematic side views of various trim-lines on a stent 46 or stent-graft 48. FIG. 7*a* illustrates a standard straight trim-line; FIG. 7*b* illustrates an angled trim-line; FIG. 7*c* illustrates a combination straight and angled trim-line; FIG. 7*d* illustrates a curved or radius trim-line and a geometric trim-line, for example, an round opening; and FIG. 7*e* illustrates a custom shape including a straight trim-line with an attached geometric trim-line. Other trim-line combinations including various geometrical shapes are envisioned.

Figure 8:
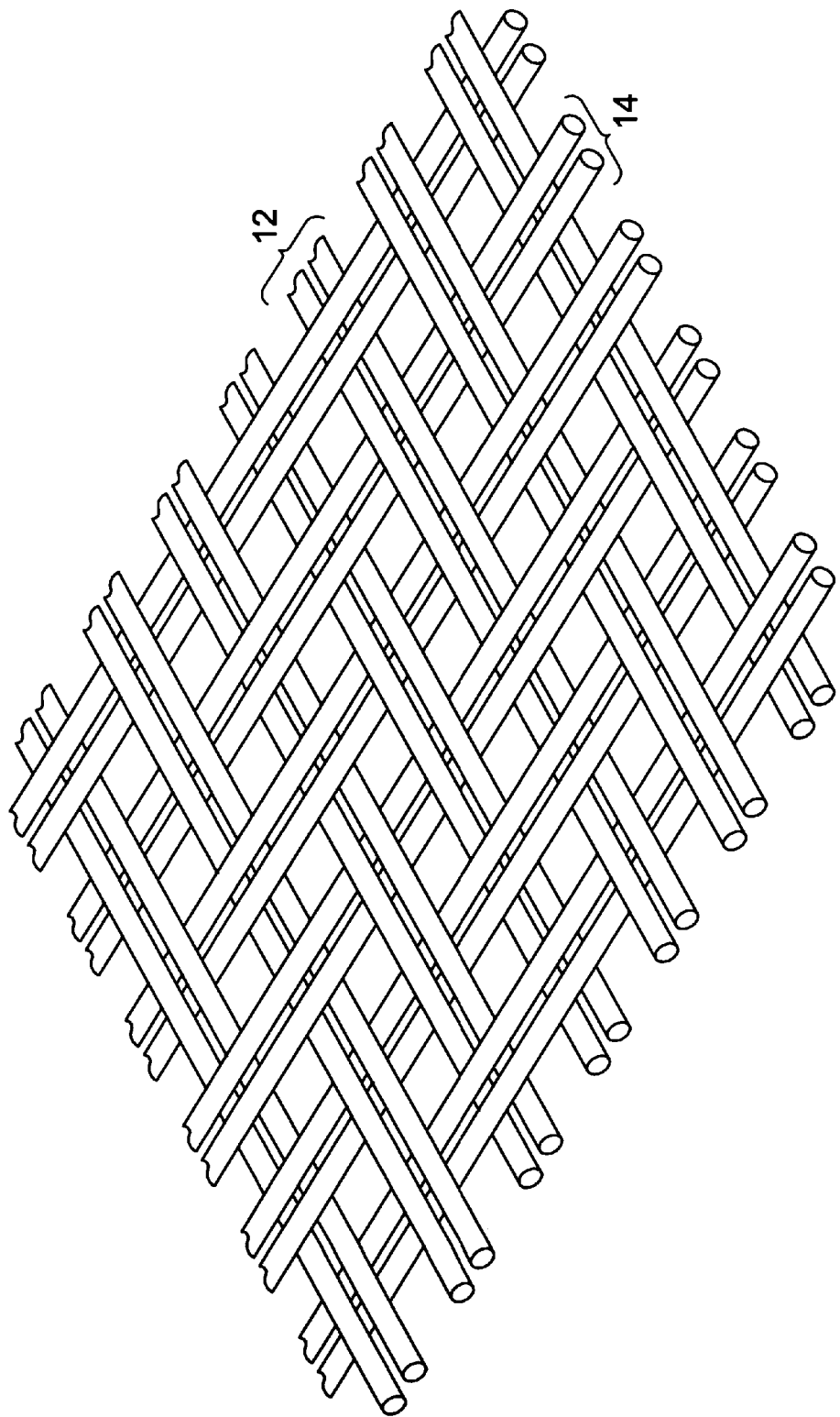
FIG. 8 is a schematic view of a 2-over-2-under braid pattern with double elongated member sets.
Figure 9:
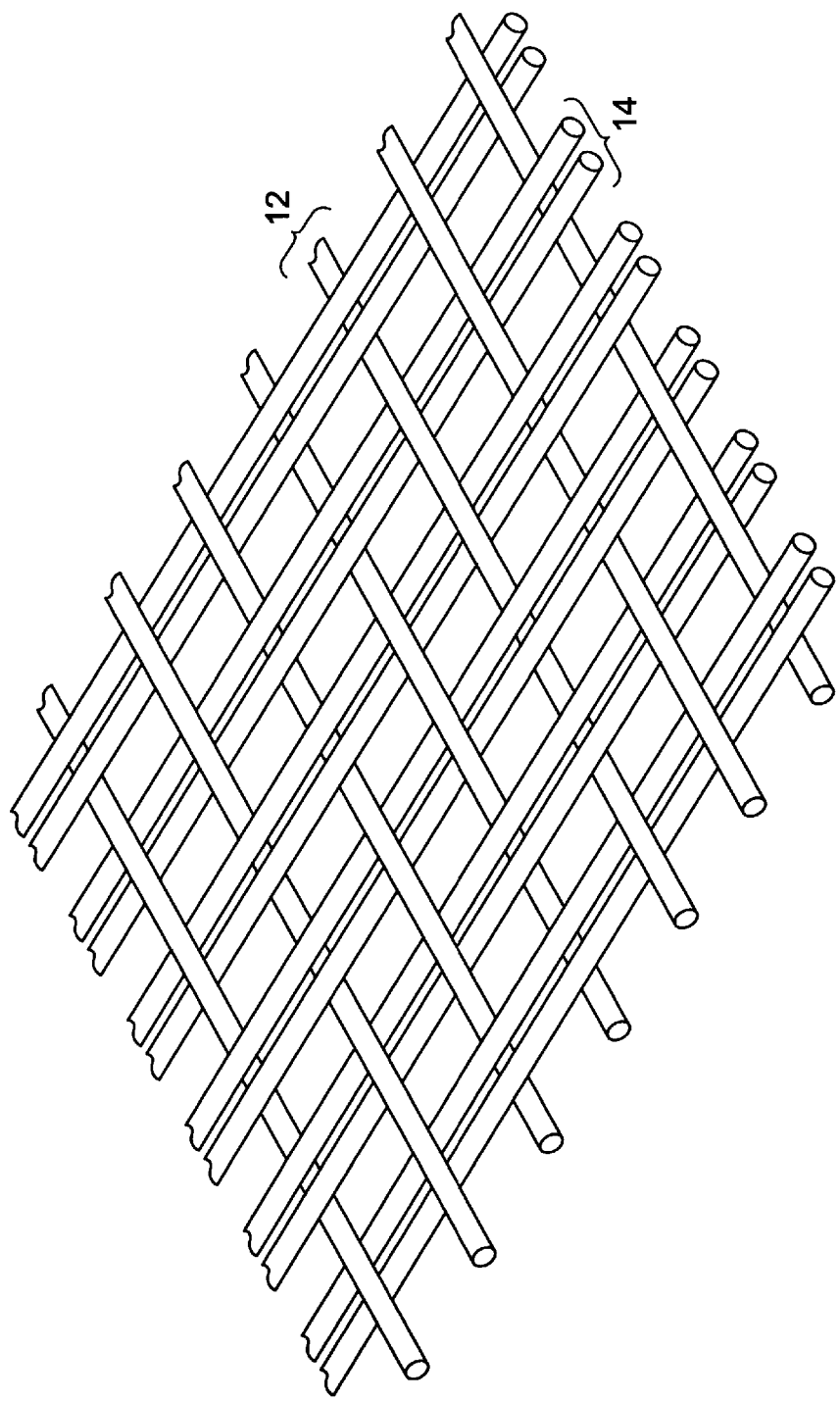
FIG. 9 is a schematic view of a 2-over-2-under braid pattern with a double elongated member set and single elongated member set.
Figure 10:
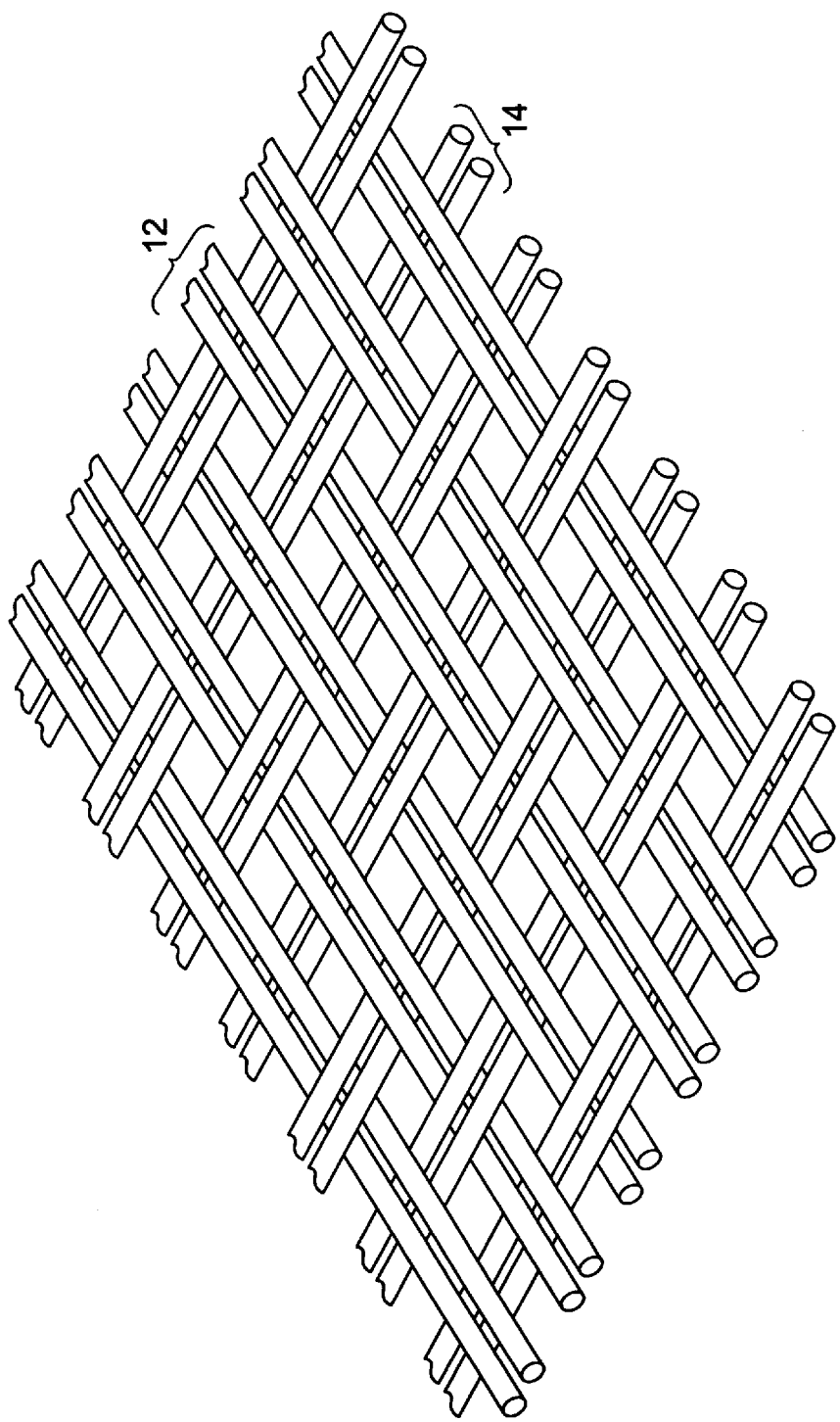
FIG. 10 is a schematic view of a 2-over-1-under braid pattern with double elongated member sets.
Figure 11:
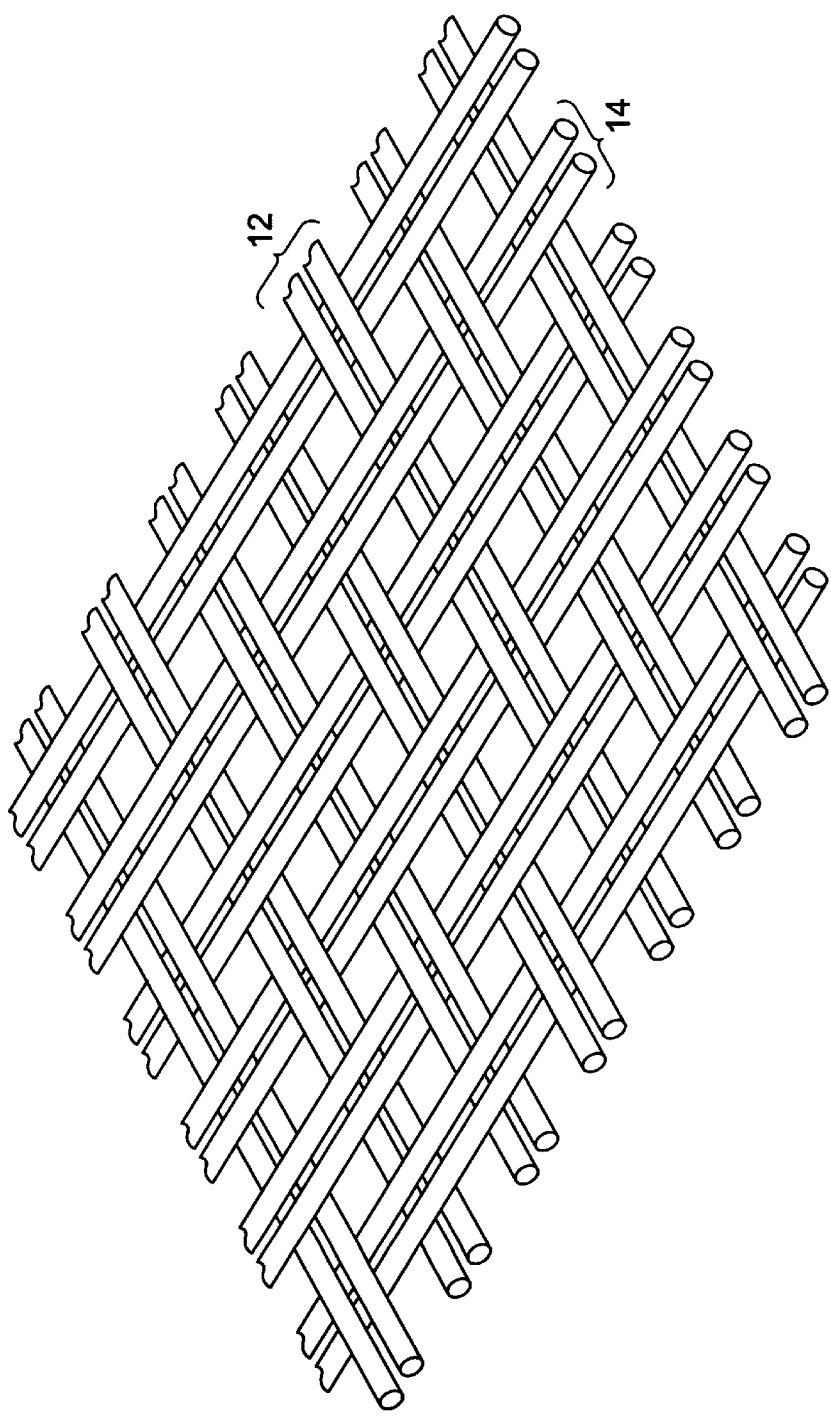
FIG. 11 is a schematic view of a 1-over-2-under braid pattern with double elongated members sets.
Figure 12:
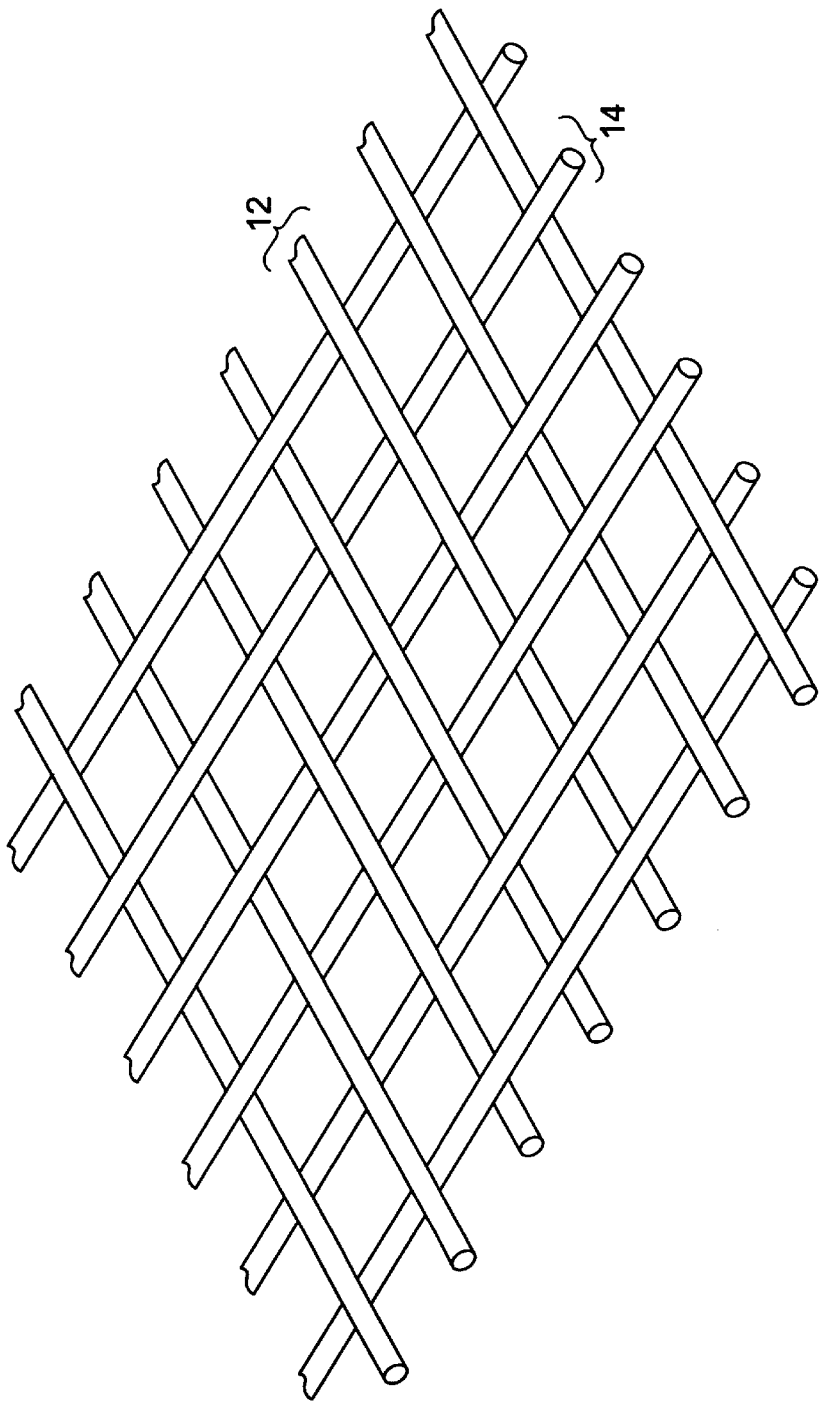
FIG. 12 is a schematic view of a 3-over-3-under braid pattern with single elongated member sets.

Various braid pattern configurations are possible. For example, FIG. 8 shows a 2-over-2-under braid pattern with double elongated member sets (double wire sets) in each direction spaced slightly apart; FIG. 9 shows a 2-over-2-under braid pattern with a double elongated member set and a single elongated member set; FIG. 10 shows a 2-over-1-under braid pattern with double elongated member sets; FIG. 11 shows a 1-over-2-under braid pattern with double elongated members sets; and FIG. 12 shows a 3-over-3-under braid pattern with single elongated member sets. Other braid pattern configurations are envisioned.

Figure 13:
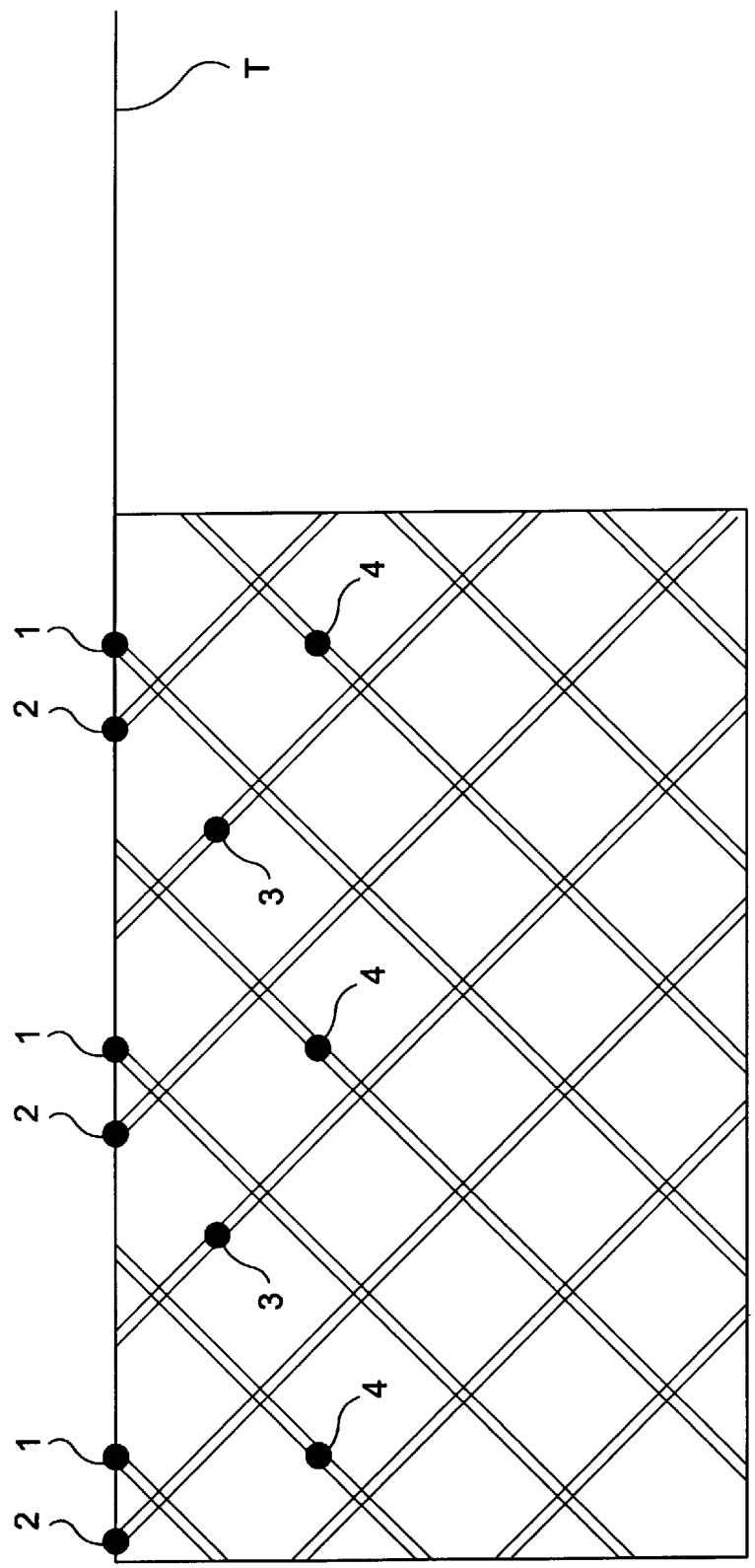
FIG. 13 is a schematic view of an end of a stent having a 2-over-2-under braid pattern, showing the trim-line and terminus.

FIG. 13 illustrates an optimum trim pattern for a 2-over-2-under braid pattern. A straight standard trim-line T and termini 1, 2, 3, 4 are shown. This is the applicable trim pattern if the member associated with each terminus 1 is formed from left to right, over the other member associated with each terminus 2 on the trim-line.

Figure 14:
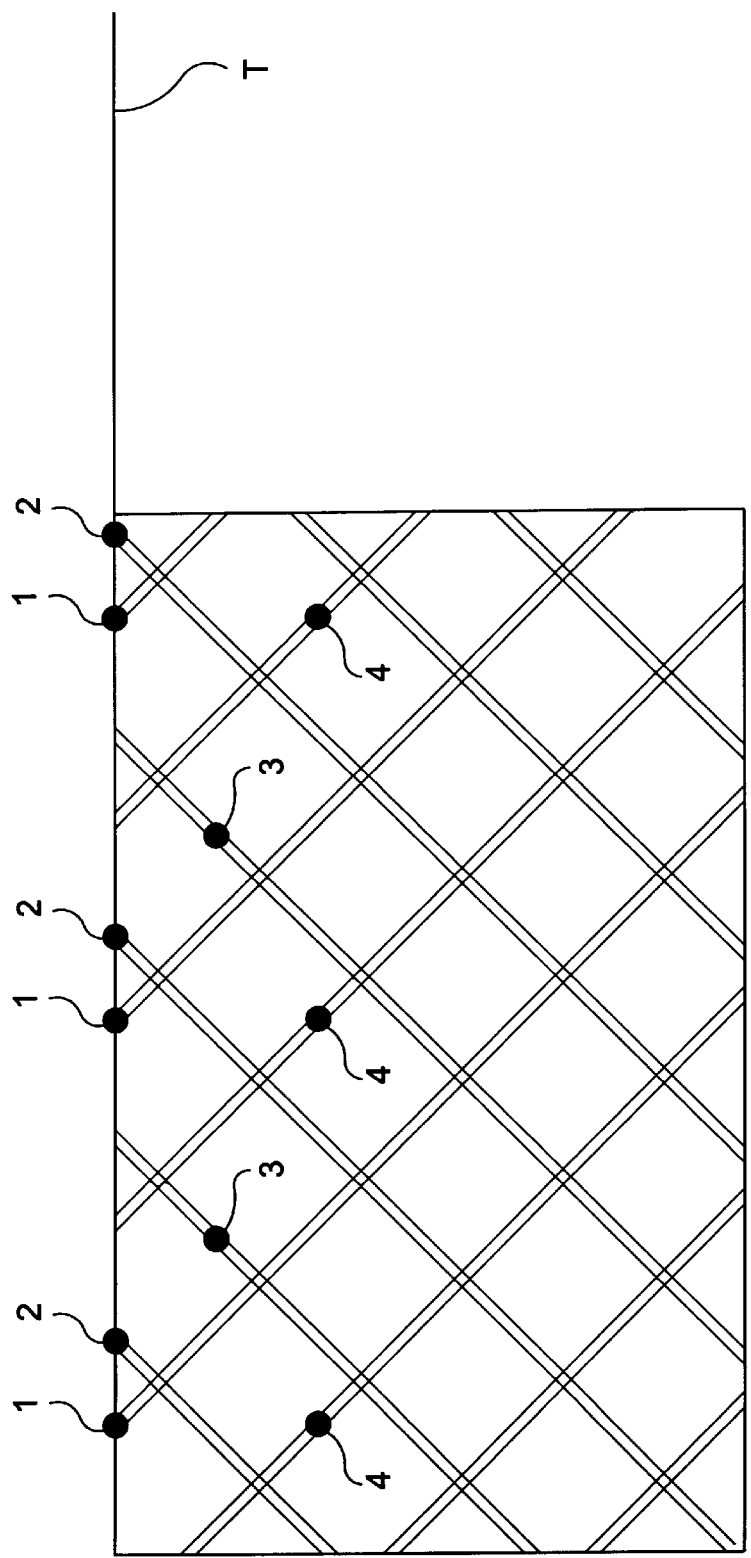
FIG. 14 is a schematic view of an inverted end of a stent having a 2-over-2-under braid pattern, showing the trim-line and terminus.

FIG. 14 illustrates an optimum trim pattern for a 2-over-2-under braid pattern. The pattern is inverted on the horizontal axis as compared to FIG. 13. A straight standard trim-line T and termini 1, 2, 3, 4 are shown. This is the applicable trim pattern if the member associated with each terminus 1 is formed from right to left, over the other member associated with each terminus 2 on the trim-line.

Figure 15A:
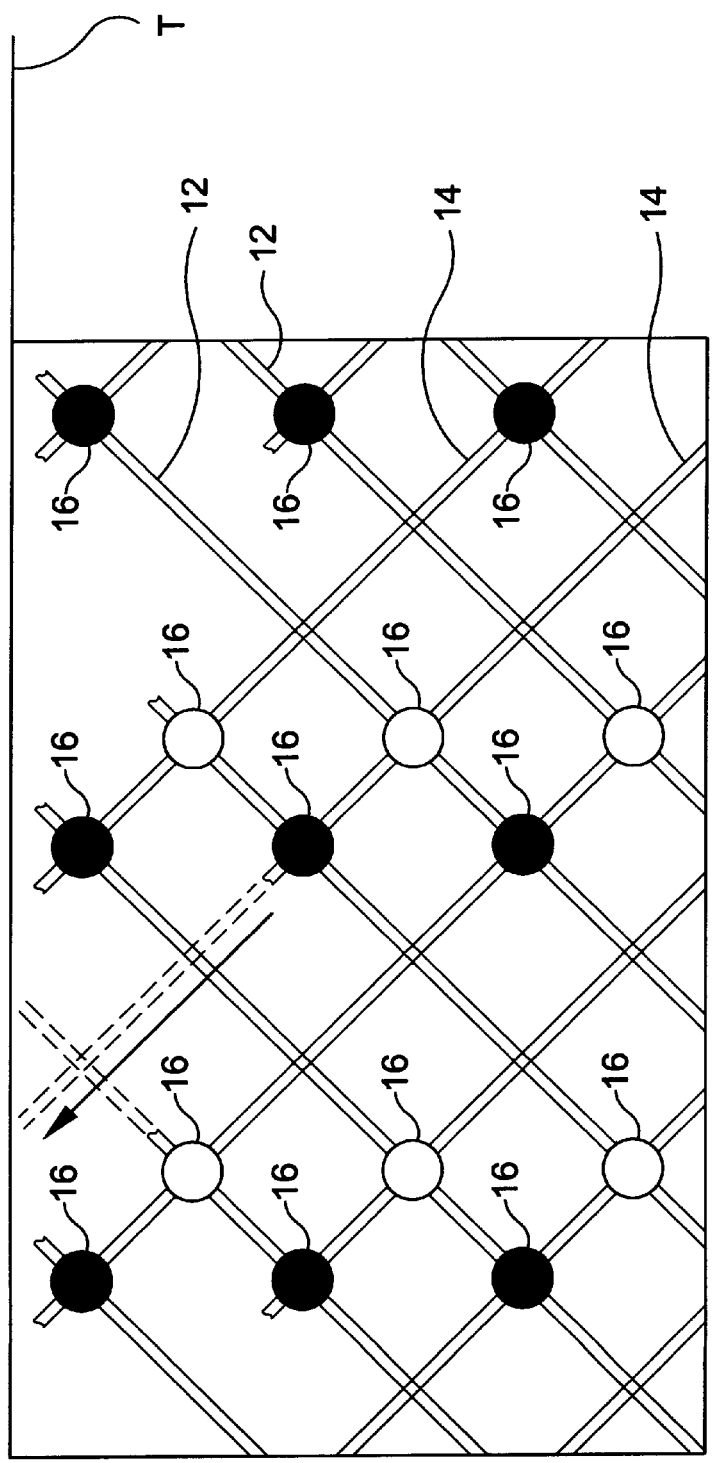
FIG. 15a is a schematic view of a portion of an end of a stent detailing the trim-line and terminus, and formation of the crown trim pattern.

FIG. 15*a* illustrates the trim-line T and termini 1, 2, 3, 4, and formation of the crown trim pattern. Control points 16 are crossing points at which an elongated member 12, 14 in the first direction crosses another elongated member 12, 14 in the second direction and one of the elongated members 12, 14 is being controlled by the other second direction member having an excess length or a distance to the control point of no greater than about one-half pic. The control points 16 shown in white indicate that the elongated members of the first direction (left to right) are supplying control to the second direction members. The control points 16 shown in black indicate the elongated members of the first direction (right to left) are supplying control to the second direction members.

As shown by the dotted lines, any excess member length, with the exception of the optimum excess length, that does not supply sufficient control to another member, i.e, does not meet the control point definition, is terminated and removed or pruned out of the braided endoprosthesis 5. Control points 16 and excess, are evaluated from the trim-line, back into the body of the structure.

Figure 15B:
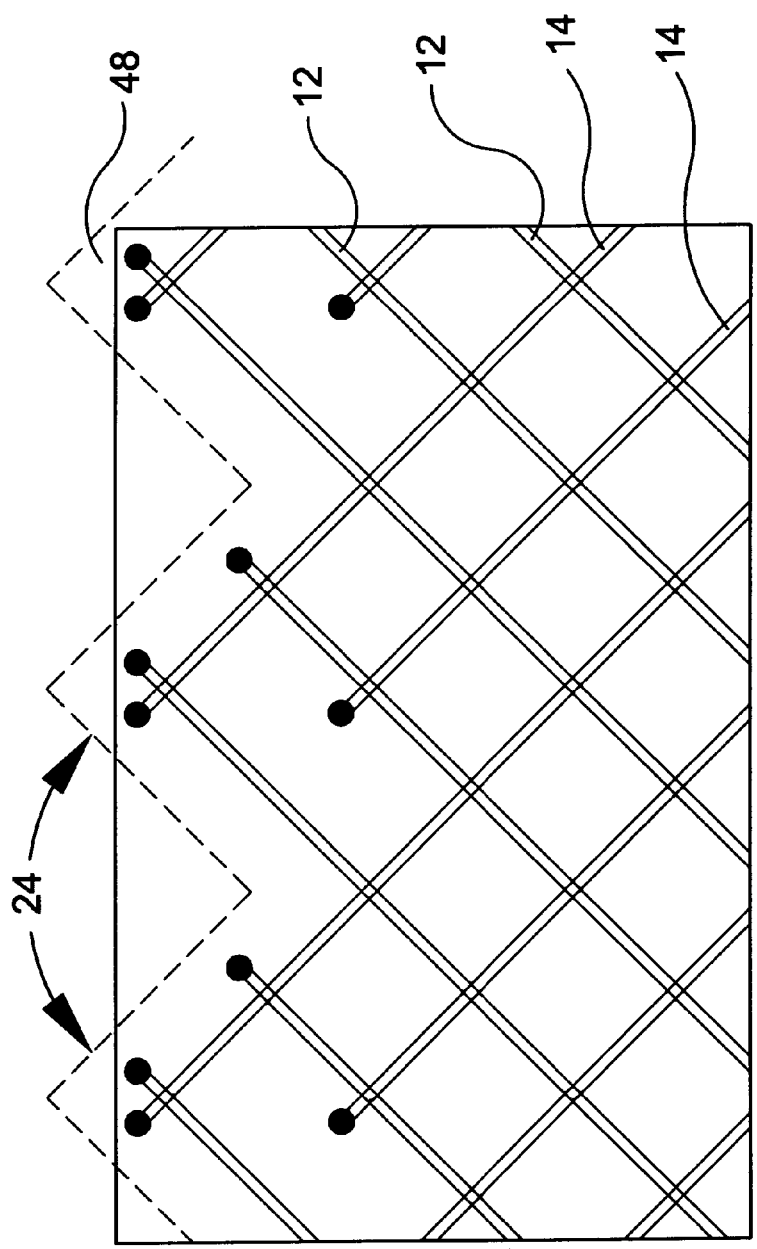
FIGS. 15b–c is a schematic view of a portion of an end of a stent detailing the trim-line and terminus, and formation of the crown trim pattern.
Figure 15C:
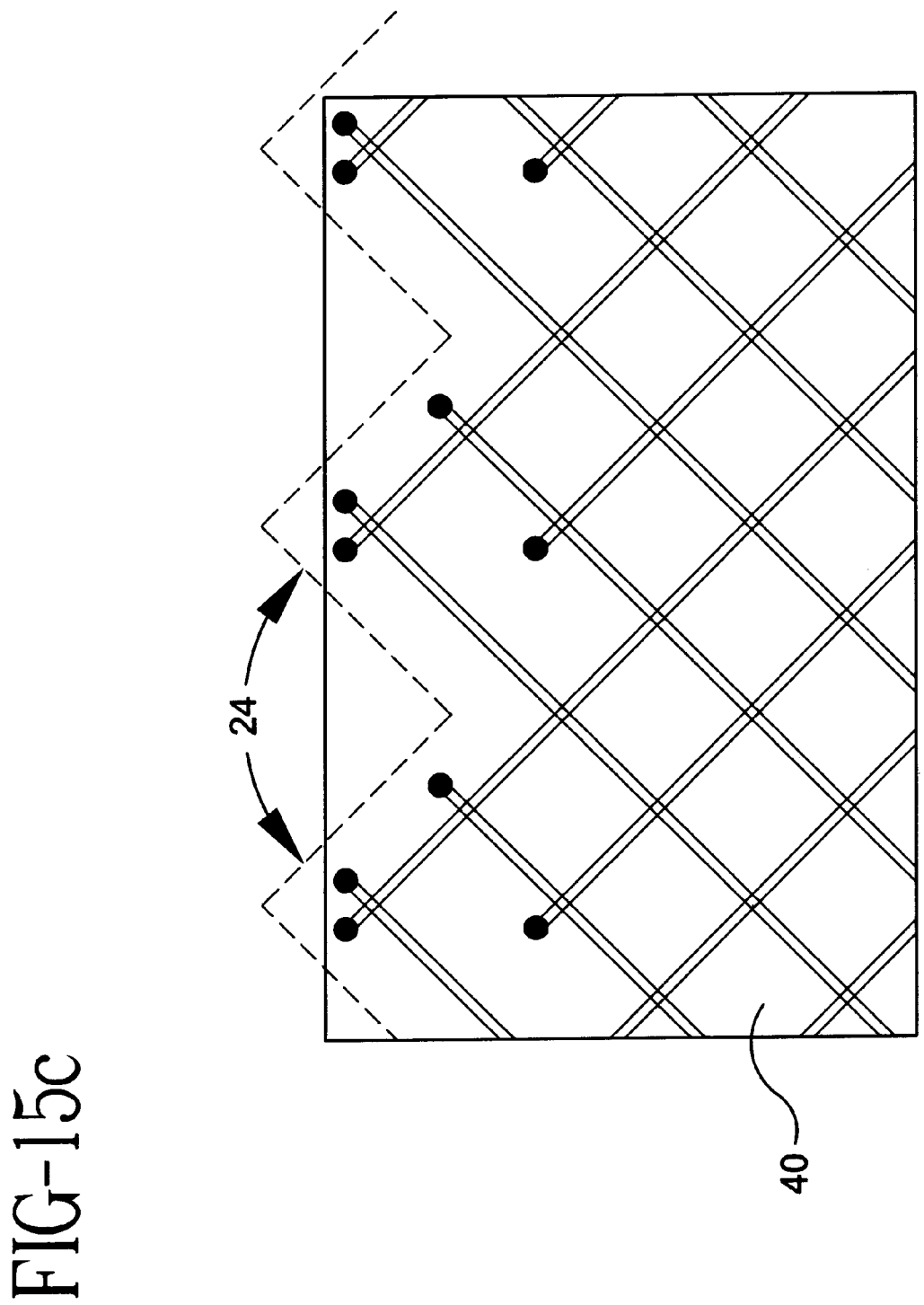

FIGS. 15*b*–*c* illustrate the trim-line and terminus 1, 2, 3, 4, and formation of the saw-tooth pattern 24 including an optional graft 48. FIG. 15*b* shows a series of termini 1, 2, 3, 4 that have been cut and removed. FIG. 15*c* shows a series of termini 1, 2, 3, 4 that have been cut and removed. Adherence of graft material is optional. The stent 46 and graft 48 are trimmed in a saw-tooth configuration from the apex of the trim-line. The graft 48 trim back is optional.

FIG. 16 is a schematic view of the crown trim pattern showing a series of cut terminus 1, 2, 3, 4 and the saw-tooth pattern 24. Also shown are trim extensions 60, 70, 80 which form in layers when the endoprosthesis is constrained in a delivery tube 50 as shown in FIG. 18.

Figure 17:
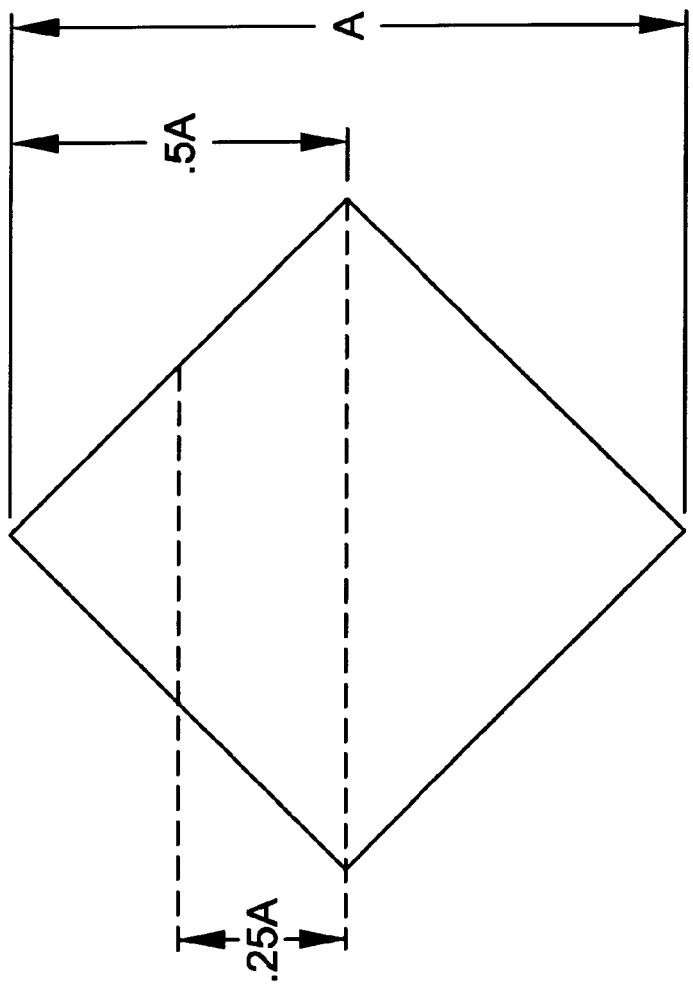
FIG. 17 illustrates a schematic view of a diamond formed by crossing elongated members and preferred terminus selection points.

FIG. 17 illustrates an individual diamond formed by crossing elongated members 12, 14 and one or more preferred terminus points 1, 2, 3, 4. Pic measurement A is equal to one Pic. The optimum length of elongated member excess from a crossing point 16 is less than one-quarter pic but greater than zero. The purpose of optimization is to keep the elongated members 12, 14 from unraveling at the crossing points 16 when constrained and expanded.

FIG. 18 illustrates a side view of an endoprosthesis in a delivery device 50 with layers 34 formed at the patterned terminated ends 10. The trim extensions 60, 70, 80 generally form layers when the endoprosthesis 5 is constrained in the delivery device 50.

A preferred method of making a braided implantable endoprosthesis 5 includes: (1) forming a first number of elongated members 12 wound helically in a first common direction and crossing a second number of elongated members 14 wound helically in a second common direction. The crossing 13 of the first and second elongated members 12, 14 defines an angle and a plurality of control points 16. The first and second elongated members 12, 14 are braided in a braid pattern greater than 1-over-1-under; (2) forming a tubular body of the first and second elongated members 12, 14 and having ends 18*a*, 18*c* and a middle portion 18*b* therebetween. The tubular body is constrainable to a reduced diameter and is self-expandable to an increased diameter; and (3) forming at least a portion of a saw-tooth pattern 24 on at least one of the ends 18*a*, 18*c* or on an edge 36 of an opening 38 in the tubular body. The saw-tooth pattern 24 is defined by a series of termini 1, 2, 3, 4, on at least one of the first or second elongated members 12, 14 at a predetermined distance from respective control points 16.

Another preferred method of making an implantable endoprosthesis includes: (1) providing a self-expanding implantable endoprosthesis 5 having a generally tubular body having ends 18*a*, 18*c* and a middle portion 18*b*. The tubular body is made of a first number of elongated members 12 wound in a first common direction and crossing a second number of elongated members 14 wound in a second common direction. The crossings 13 of the first and second elongated members 12, 14 define an angle therebetween and a plurality of control points 16. The first and second elongated members 12, 14 are braided in a braid pattern configuration greater than 1-over-1-under. The tubular body is constrainable to a reduced diameter and is self-expandable to an increased diameter; identifying a trim-line T through the tubular body; (2) cutting the one or more elongated members 12, 14 at one or more termini 1, 2, 3, 4 that intersect the trim-line T; and (3) cutting the one or more elongated members 12, 14 at termini 1, 2, 3, 4 where the one or more elongated members 1, 2, 3, 4 do not substantially control another elongated member 12, 14 to form a substantially saw-tooth pattern 24 along the trim-line T. The method may further include constraining the tubular body to orient one or more elongated members 12, 14 in a substantially longitudinal direction and in two or more layers 34. The method may further include disposing a graft 40 on one or more surfaces 42, 44 or between elongated members 12, 14 of the implantable endoprosthesis 5. An implantable endoprosthesis 5 is formed by the method.

Similar or additional methods for other braid patterns greater than 1-over-1-under and including a plurality of paired members are also envisioned.

Termination of an elongated filament (terminus 1, 2, 3, 4) is preferably performed in one step, regardless of the numbers of parallel elongated members 12, 14 or physical makeup of the member 12, 14.

A method for patterned termination of a trim-line T for stents 46 or stent-grafts 48 using a 2-over-2-under braiding pattern and an even number of paired members is described below.

1. Study the braid diagram of the stent 46 such as a paired member pattern with a 2-over-2-under braid pattern. Follow the paired member to confirm the paired member pattern. The termini to be cut are 1, 2, 3 and 4. The terminus 4 and terminus 3 member pairs will be cut before the stent 46 is placed over a liner or graft 48. The terminus 1, 2 member pairs will be cut after the stent 46 is attached to the liner or graft 48.
2. Place the stent 46 in a measuring guide tube of a predetermined size such that the proximal flare end 18a sticks above the tube and is in contact with the inner diameter of the tube at the rim. Check that the distal end 18c does not get hung up on a centering ring.
3. Locate the terminus 4 member pair closest to the inner diameter of the guide tube. The center cutting point is after this member goes over the terminus 3 member pair.
4. Pull the stent 46 out of the guide just enough to be able to cut the terminus 4 member pair and make the cut about ⅓ pic above the cross-over point using cutters. The cut is made by placing the cutters handle nearly parallel to the member, and making a square cut on the member.
5. Follow the terminus 4 member pair two picks above and make another cut, removing a section of this member pair.
6. Return to the initial terminus 4 point, count four member pairs to the left or right and your next terminus 4 member pair will be located. Confirm that it is an "over" member and repeat the terminus 4 cut first at the bottom then two pics above, following that member.
7. Continue this process until all terminus 4 cuts are made and member sections removed.
8. Locate any first terminus 3 member pair and cut the terminus 3 member pair ⅓ pic above the cross-over point as shown in the diagram. Follow that member two pics above and make another cut, removing this section of member.
9. Return to the initial terminus 3 point, count four member pairs to the left or right and your next terminus 3 member pair will be located. Confirm that it is an "over" member pair and repeat the terminus 3 cut first at the bottom then two pics above following that member pair.
10. Continue this process until all terminus 3 cuts are made and member sections removed.

Alternatively, perform a terminus 4 cut and terminus 3 cut by following steps 4–6 and then steps 8–9 in an alternate fashion.

11. When finished, the stent 46 will be held by the terminus 1 and terminus 2 paired members and will appear like diamond shape holes, all around. Make sure that the terminus 3 and terminus 4 members are in the appropriate over/under pattern, and inspect for any loose member pieces.

Additional steps for a stent having a graft attached may include the following steps:

1. After the liner is salt packed, cured, washed and dried, the final series of terminus 1 and terminus 2 cuts is made to trim off the proximal flare.
2. First, trim off the excess proximal flare using scissors cutting parallel to the axis 22 of the stent 46 and then perpendicular to the axis leaving about 2–3 picks worth of excess flare above the terminus 1 and terminus 2 cut points.
3. Using the cutters, cut the terminus 1 and terminus 2 paired members cutting the liner with it. Repeat this process until all terminus 1 and terminus 2 member pairs are cut.
4. Finally, trim off the liner or graft 48 using the cutters. At this step, some of the members can be trimmed to be close to about ⅓ pic from the crossover point.
5. Perform a final length cut at the distal end using scissors by measuring, for example for a 27 mm diameter device, about 120 mm±5 mm from the apex of the crown cut using a ruler.
6. Perform an inspection to assure all cuts were properly made and that no pair ends have become untapped or twisted such that they will not collapse correctly.

Inspection should be performed with either a magnifying lens or the stereo microscope.

While a particular preferred embodiment has been illustrated and described the scope of protection sought is in the claims that follow.

What is claimed is:

1. A braided implantable endoprosthesis including:
    a first number of elongated resilient first members wound helically in a first common direction, and a second number of elongate resilient second members wound in a second common direction different than the first common direction, and braided together with the first members in a braid pattern other than 1-over-1-under, to form a tubular body constrainable to a reduced diameter and self-expandable to an increased diameter, said tubular body having opposite first and second end edges;
    wherein the first members and the second members form multiple crossing points each comprised of a crossing member pair including a first member and a second member, each member of the pair contacting the other and being free for a limited sliding with respect to the other;
    wherein the crossing points include control points at which one of the members of the pair supplies sufficient control to the other member of the pair, and non-control pairs at which neither member of the pair supplies sufficient control to the other;

a first trim extension including a first series of edge terminae, formed in the first and second members and defining a portion of said first end edge of the tubular body, wherein each of the edge terminae is spaced at a pre-determined distance from its nearest crossing point; and a second trim extension including a second series of terminae of at least one of the first members and the second members, wherein the second trim extension is spaced apart from the first trim extension in an axially inward direction with respect to the tubular body by a depth in said axial direction of at least one pic.

2. The endoprosthesis of claim 1 wherein:
each of the terminae of said second trim extension is spaced at said predetermined distance from its nearest one of said crossing points.

3. The endoprosthesis of claim 2 wherein:
each of said crossing points nearest one of the terminae of the second trim extension is a control point.

4. The endoprosthesis of claim 3 wherein:
said pre-determined distance is less than about one-half pic.

5. The endoprosthesis of claim 4 wherein:
said pre-determined distance is about one-third pic.

6. The endoprosthesis of claim 1 wherein:
the terminae of the first trim extension and the second extension cooperate to form a saw-tooth pattern of said first end edge to substantially orient a plurality of the first members and second members in a substantially similar longitudinal direction when the tubular body is in a constrained diameter.

7. The endoprosthesis of claim 6 wherein:
the saw-tooth pattern is adapted to align the first and second members.

8. The endoprosthesis of claim 1 wherein:
said longitudinal depth increases as the braid pattern increases.

9. The endoprosthesis of claim 1 wherein:
the braid pattern is selected from the group of braid patterns consisting of: 2-over-2-under; 2-over-1-under; 1-over-2-under; 3-over-3-under; 3-over-2-under; 2-over-3-under; 3-over-1-under; 1-over-3-under; 4-over-4-under; 4-over-3-under; 3-over-4-under; 4-over-2-under; 2-over-4-under; 4-over-1-under; 1-over-4-under; 5-over-5-under; 5-over-4-under; 5-over-4-under; 4-over-5-under; 5-over-3-under; 3-over-5-under; 5-over-2-under; 2-over-5-under; 5-over-1-under; and 1-over-5-under.

10. The endoprosthesis of claim 9 wherein:
the braid pattern is 2-over-2-under, and said depth is about one pic.

11. The endoprosthesis of claim 9 wherein:
the braid pattern is 3-over-3-under, and the depth is about two pics.

12. The endoprosthesis of claim 9 wherein:
the braid pattern is 4-over-4-under, and the depth is about three pics.

13. The endoprosthesis of claim 1 wherein:
at least one of the first and second members includes a plurality of elongated members substantially parallel to one another.

14. The endoprosthesis of claim 1 wherein:
said first number and said second number are less than 11.

15. The endoprosthesis of claim 1 wherein:
said second number is different than the first number.

16. The endoprosthesis of claim 1 wherein:
said tubular body is greater in diameter at the first end edge than along a middle portion thereof.

17. The endoprosthesis of claim 1 wherein:
the tubular body is made of at least one material selected from the group of materials consisting of: metals, plastics, bioabsorbable materials, synthetic materials, and natural materials.

18. The endoprosthesis of claim 1 wherein:
the first and second common directions are substantially opposite, and the first and second members form a braid angle between 65 degrees and 155 degrees.

19. A process for making a braided implantable endoprosthesis, including:

braiding a first number of elongated resilient first members together with a second number of elongated resilient second members in a braid pattern other than 1-over-1-under, and in which the first and second members are wound helically in first and second different respective common directions thereby forming multiple crossing points each comprised of a member pair including one first member and one second member, thus to form a tubular body having opposite first and second end edges and a middle portion between the end edges, the tubular body being constrainable to a reduced diameter and self-expandable to an increased diameter;

selectively cutting the first and second members to form a first trim extension comprising a series of first edge terminae to define a portion of the first end edge of the tubular body, wherein the first and second members are selectively cut to position each of the first edge terminae at a pre-determined distance from its nearest crossing point; and further, selectively cutting at least one of the first members and the second members to form a second trim extension comprising a second series of edge terminae, and further to position the second trim extension inwardly of the first trim extension, spaced apart longitudinally with respect to the tubular body from the first trim extension by a depth of at least one pic.

20. The process of claim 19 further including:
examining the crossing points and identifying as control points certain ones of the crossings at which one of the member pair supplies sufficient control to the other member of the pair; and wherein said further selective cutting to form the second trim extension comprises forming all the terminae of the second series spaced at said pre-determined distance from one of the control points.

21. The process of claim 20 wherein:
said selective cutting to form the second trim extension consists essentially of cutting the first members.

22. The process of claim 21 further including:
selectively cutting the second members to form a third trim extension including a third series of terminae, wherein the third trim extension is spaced longitudinally from the first trim extension and the second extension, and is disposed between the first and second trim extensions.

23. The process of claim 22 wherein:
each terminus of the first, second and third trim extensions is spaced apart from its nearest crossing point by said pre-determined distance.

24. The process of claim 23 wherein:

said pre-determined distance is less than one-half pic.

25. A process for making an implantable endoprosthesis, including:

providing a longitudinally extending tubular body having opposite end edges and a middle portion between the edges, the tubular body being formed of a first number of elongated first members wound in a first common direction and a second number of elongated second members wound in a second common direction different than the first common direction, wherein the first and second members are braided in a braid pattern other than 1-over-1-under to form multiple crossing points, and wherein the tubular body is constrainable to a reduced diameter and tends to self-expand to an increased diameter when not constrained;

cutting the first members and second members along a trim line, to form in the first and second members a series of terminae along the trim line;

examining the crossing points to identify certain ones of the crossing points as control points where at least one member of a member pair at the crossing point supplies sufficient control to the other member of the member pair; and trimming at least one of the first members and the second members proximate at least selected ones of the control points, to form a first trim extension including a series of terminae and spaced apart from the trim line in the longitudinal direction inwardly of the trim line by a depth of at least one pic.

26. The process of 25 further including:

disposing a graft on one or more surfaces of the tubular body.

27. An implantable endoprosthesis formed by the process of claim 25.

28. A braided implantable endoprosthesis comprising:

a first set of resilient elongated first members wound helically in a first direction, and a second set of resilient elongated second members wound helically in a second direction different than the first direction, and braided with the first members in a braid pattern of at least 1-over-1-under to form multiple crossing points to form a tubular body having opposite end edges and a middle portion there between, said tubular body being constrainable to a reduced diameter and tending to self-expand to an increased diameter when not constrained;

wherein each of the crossing points is formed by a member pair including one of the first members and one of the second members, in contact with one another and slidable with respect to one another;

a first trim extension including a first series of terminae of the first and second members defining at least a portion of the first end edge of the tubular body, each terminus of the first trim extension being spaced apart from its nearest one of the crossing points by a pre-determined distance; and a second trim extension including a second series of terminae of at least one of the first members and the second members, said second trim extension being spaced longitudinally inwardly of the first trim extension by a longitudinal depth of at least one pic, wherein each terminus of the second trim extension is spaced apart from its nearest one of the crossing points by at most said pre-determined distance.

29. the braided implantable endoprosthesis of claim 28 further comprising:

a graft material disposed on at least a portion of a surface of the tubular body.

* * * * *